United States Patent [19]

Dube et al.

[11] Patent Number: 6,071,936

[45] Date of Patent: *Jun. 6, 2000

[54] SUBSTITUTED PYRIDINES AS SELECTIVE CYCLOOXYGENASE-2 INHIBITORS

[75] Inventors: Daniel Dube, St. Lazare; Rejean Fortin, Montreal-Nord; Richard Friesen, Dollard Des Ormeaux; Zhaoyin Wang, Pierrefonds; Jacques Yves Gauthier, Laval, all of Canada

[73] Assignee: Merck Frosst Canada & Co., Kirkland, Canada

[*] Notice: This patent is subject to a terminal disclaimer.

[21] Appl. No.: 09/312,790

[22] Filed: May 17, 1999

Related U.S. Application Data

[62] Division of application No. 08/893,395, Jul. 11, 1997, Pat. No. 5,861,419, which is a division of application No. 09/181,887, Oct. 29, 1998, Pat. No. 6,001,843

[60] Provisional application No. 60/022,128, Jul. 18, 1996, provisional application No. 60/027,139, Oct. 1, 1996, and provisional application No. 60/041,814, Apr. 8, 1997.

[51] Int. Cl.[7] ........................ A61K 31/444; C07D 213/44
[52] U.S. Cl. .......................... 514/334; 546/257; 546/258
[58] Field of Search ............................ 514/334; 546/257, 546/258

[56] References Cited

U.S. PATENT DOCUMENTS

| | | | |
|---|---|---|---|
| 5,593,994 | 1/1997 | Batt | 514/252 |
| 5,596,994 | 1/1997 | Batt | 128/732 |
| 5,861,419 | 1/1999 | Dube | 514/334 |
| 5,932,586 | 8/1999 | Batt | 514/277 |

*Primary Examiner*—D. Margaret Seaman
*Attorney, Agent, or Firm*—Richard C. Billups; David L. Rose

[57] ABSTRACT

The invention encompasses the novel compound of Formula I as well as a method of treating COX-2 mediated diseases comprising administration to a patient in need of such treatment of a non-toxic therapeutically effective amount of a compound of Formula I.

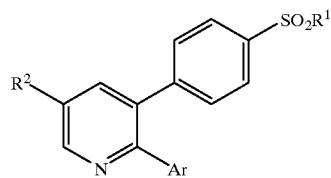

The invention also encompasses certain pharmaceutical compositions for treatment of COX-2 mediated diseases comprising compounds of Formula I.

19 Claims, No Drawings

SUBSTITUTED PYRIDINES AS SELECTIVE CYCLOOXYGENASE-2 INHIBITORS

CROSS REFERENCE TO RELATED APPLICATIONS

This application is a division of U.S. application Ser. No. 08/893,395 filed on Jul. 11, 1997, now U.S. Pat. No. 5,861,419 granted on Jan. 19, 1999, and U.S. application Ser. No. 09/181,887 filed on Oct. 29, 1998, now U.S. Pat. No. 6,001,843, and copending herewith, based upon Provisional Application Nos. 60/022,128 filed on Jul. 18, 1996, 60/027,139 filed on Oct. 1, 1996 and 60/041,814 filed on Apr. 8, 1997, priority of which is claimed hereunder.

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

The potential utilities of selective cyclooxygenase-2 inhibitors are discussed in the following articles:

1. John Vane, "Towards a better aspirin" in *Nature,* Vol. 367, pp. 215–216, 1994.
2. Bruno Battistini, Regina Botting and Y. S. Bakhle, "COX-1 and COX-2: Toward the Development of More Selective NSAIDs" in *Drug News and Perspectives,* Vol. 7, pp. 501–512, 1994.
3. David B. Reitz and Karen Seibert, "Selective Cyclooxygenase Inhibitors" in *Annual Reports in Medicinal Chemistry,* James A. Bristol, Editor, Vol. 30, pp. 179–188, 1995.
4. Don E. Griswold and Jerry L. Adams, "Constituative Cyclooxygenase (COX-1) and Inducible Cyclooxygenase (COX-2): Rationale for Selective Inhibition and Progress to Date" in *Medicinal Research Reviews,* Vol. 16, pp. 181–206, 1996.

WO 96/10012 (DuPont Merck, Apr. 4, 1996) discloses compounds represented by Formula A as being useful in the treatment of COX-2 mediated diseases, by virtue of their selective inhibition of COX-2 rather than COX-1. We have now discovered that a subset of the compounds represented by A, in which —J—K—L— is —NCHCH—, X is a bond, $R^1$ is aromatic and $R^3$ and $R^4$ are not both hydrogen show unexpectedly superior selectivity for the inhibition of COX-2 over COX-1 and/or superior potency as compared to the closest species disclosed in 96/10012. This subset of compounds is the subject of the present invention and is represented by Formula I.

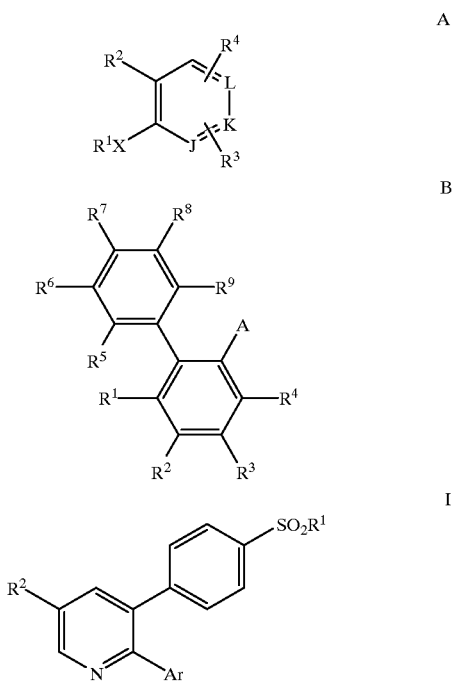

Of the over 175 specific compounds disclosed in WO 96/10012, only 4 of them are pyridines, and none of these latter contain a substituent ($R^3$ or $R^4$ in A) on the pyridine ring.

WO 96/16934 (Searle, Jun. 6, 1996) discloses compounds represented by structure B as being useful for the treatment of inflammation and related disorders. Chemically, these compounds differ from those of the present invention in that the central of the three aromatic rings is benzene rather than pyridine.

SUMMARY OF THE INVENTION

The invention encompasses the novel compound of Formula I as well as a method of treating COX-2 mediated diseases comprising administration to a patient in need of such treatment of a non-toxic therapeutically effective amount of a compound of Formula I.

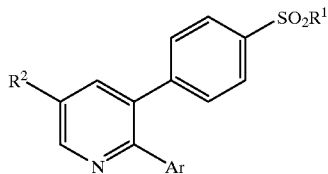

The invention also encompasses certain pharmaceutical compositions for treatment of COX-2 mediated diseases comprising compounds of Formula I.

DETAILED DESCRIPTION OF THE INVENTION

The invention encompasses the novel compound of Formula I as well as a method of treating COX-2 mediated diseases comprising administration to a patient in need of such treatment of a non-toxic therapeutically effective amount of a compound of Formula I

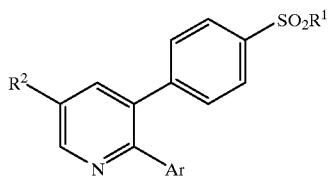

wherein:
$R^1$ is selected from the group consisting of
(a) $CH_3$,
(b) $NH_2$,
(c) $NHC(O)CF_3$,
(d) $NHCH_3$;
Ar is a mono-, di-, or trisubstituted phenyl or pyridinyl (or the N-oxide thereof), wherein the substituents are chosen from the group consisting of
(a) hydrogen,
(b) halo,
(c) $C_{1-6}$alkoxy,
(d) $C_{1-6}$alkylthio,
(e) CN,
(f) $C_{1-6}$alkyl,
(g) $C_{1-6}$fluoroalkyl,
(h) $N_3$,
(i) —$CO_2R^3$,
(j) hydroxy,
(k) —$C(R^4)(R^5)$—OH,
(l) —$C_{1-6}$alkyl-$CO_2$—$R^6$,
(m) $C_{1-6}$fluoroalkoxy;
$R^2$ is chosen from the group consisting of
(a) halo,
(b) $C_{1-6}$alkoxy,
(c) $C_{1-6}$alkylthio,
(d) CN,
(e) $C_{1-6}$alkyl,
(f) $C_{1-6}$fluoroalkyl,
(g) $N_3$,
(h) —$CO_2R^7$,
(i) hydroxy,
(j) —$C(R^8)(R^9)$—OH,
(k) —$C_{1-6}$alkyl-$CO_2$—$R^{10}$,
(l) $C_{1-6}$fluoroalkoxy,
(m) $NO_2$,
(n) $NR^{11}R^{12}$, and
(o) $NHCOR^{13}$,
$R^3$, $R^4$, $R^5$, $R^6$, $R^7$, $R^8$, $R^9$, $R^{10}$, $R^{11}$, $R^{12}$, $R^{13}$, are each independantly chosen from the group consisting of
(a) hydrogen, and
(b) $C_{1-6}$alkyl,
or $R^4$ and $R^5$, $R^8$ and $R^9$ or $R^{11}$ and $R^{12}$ together with the atom to which they are attached form a saturated monocyclic ring of 3, 4, 5, 6 or 7 atoms.

Apt alkyl groups include methyl, ethyl, n-propyl, iso-propyl and butyl, pentyl and hexyl groups. A favoured alkyl group is the methyl group. In general $R^4$ and $R^5$, $R^8$ and $R^9$ and $R^{11}$ and $R^{12}$ are not residues of the above-mentioned monocyclic rings. When 'alkyl' is part of a composite term such as alkoxy, alkylthio, fluoroalkyl, fluoroalkoxy then the above meaning of alkyl refers also to the composite term.

A preferred sub-genus of formula I is that wherein Ar is a mono-, or disubstituted pyridinyl. Within this sub-genus, the 3-pyridinyl isomers, such as those of formula Ic, are particularly preferred.

When Ar is di-substituted phenyl is particularly apt that one or both of the substituents are hydrogen.

Another preferred sub-genus of formula I is that wherein Ar is a mono- or disubstituted phenyl.

When Ar is di-substituted phenyl it is particularly apt that one of the substituents is hydrogen or fluorine and the second is hydrogen, fluorine, chlorine, methyl, methoxyl or trifluoromethyl.

Another preferred sub-genus of formula I is that wherein $R^1$ is $CH_3$ or $NH_2$. Generally, $CH_3$ is preferred for COX-2 specificity and $NH_2$ is preferred for potency.

Another preferred sub-genus of formula I is that wherein $R^2$ is halo, $CH_3$ or $CF_3$.

Another preferred sub-genus of formula I is that wherein the substituents on Ar are chosen from the group consisting of
(a) hydrogen,
(b) halo,
(c) $C_{1-4}$alkoxy,
(d) $C_{1-4}$alkylthio,
(e) $C_{1-4}$alkyl,
(f) $CF_3$, and
(g) CN.

In one aspect the invention is directed to compounds of formula I

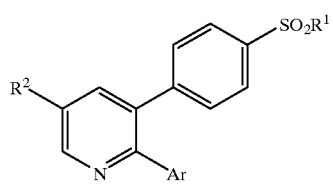

wherein:
R¹ is selected from the group consisting of
(a) CH₃,
(b) NH₂,
(c) NHC(O)CF₃,
(d) NHCH₃;
Ar is a mono-, di-, or trisubstituted pyridinyl (or the N-oxide thereof), wherein the substituents are chosen from the group consisting of
(a) hydrogen,
(b) halo,
(c) $C_{1-6}$alkoxy,
(d) $C_{1-6}$alkylthio,
(e) CN,
(f) $C_{1-6}$alkyl,
(g) $C_{1-6}$fluoroalkyl,
(h) $N_3$,
(i) —$CO_2R^3$,
(j) hydroxy,
(k) —$C(R^4)(R^5)$—OH,
(l) —$C_{1-6}$alkyl-$CO_2$—$R^6$,
(m) $C_{1-6}$fluoroalkoxy;
R² is chosen from the group consisting of
(a) halo,
(b) $C_{1-6}$alkoxy,
(c) $C_{1-6}$alkylthio,
(d) $C_{1-6}$alkyl,
(e) $N_3$,
(f) —$CO_2H$,
(g) hydroxy,
(h) $C_{1-6}$fluoroalkoxy,
(i) $NO_2$,
(j) $NR^{11}R^{12}$, and
(k) $NHCOR^{13}$,
$R^3$, $R^4$, $R^5$, $R^6$, $R^{11}$, $R^{12}$, $R^{13}$, are each independantly chosen from the group consisting of
(a) hydrogen, and
(b) $C_{1-6}$alkyl,
or $R^4$ and $R^5$ or $R^{11}$ and $R^{12}$ together with the atom to which they are attached form a saturated monocyclic ring of 3, 4, 5, 6 or 7 atoms.

Within this aspect there is a genus of compounds of formula

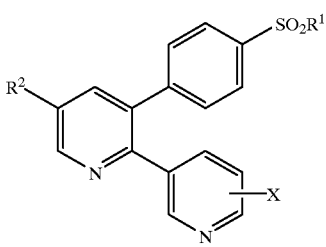

Ic wherein:
R¹ is selected from the group consisting of
(a) CH₃,
(b) NH₂,
R² is chosen from the group consisting of
(a) chloro,
(b) methyl,
and wherein there may be one, two or three groups X independently selected from the group consisting of
(a) hydrogen,
(b) halo,
(c) $C_{1-4}$alkoxy,
(d) $C_{1-4}$alkylthio,
(e) CN,
(f) $C_{1-4}$alkyl,
(g) CF3.

Within this genus of compounds of formula Ic

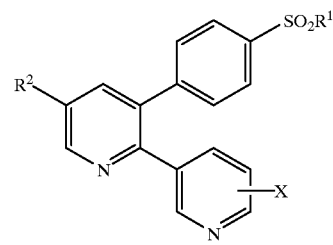

Ic there is a sub-genes wherein:
R¹ is selected from the group consisting of
(a) CH₃,
(b) NH₂,
R² is chloro,
wherein there is one group X independently selected from the group consisting of
(a) hydrogen,
(b) F or Cl,
(c) methyl,
(d) ethyl.

Within this genus of compounds of formula Ic

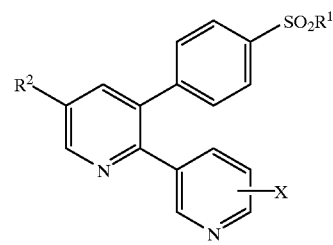

Ic there is a sub-genes wherein:
R¹ is selected from the group consisting of
(a) CH₃,
(b) NH₂,
R² is chloro,
wherein there is one group X independently selected from the group consisting of
(a) hydrogen,
(b) F or Cl,
(c) methyl.

Preferred compounds of formula I and Ic include those wherein R² is halo, especially chloro.

Preferred compounds of formula I and Ic include those wherein Ar is 3-pyridinyl and X is hydrogen or $C_{1-3}$alkyl, especially hydrogen, p-methyl and p-ethyl.

Illustrating the invention are the following compounds:
3-(4-Methylsulfonyl)phenyl-2-phenyl-5-trifluoromethylpyridine;
2-(3-Chlorophenyl)-3-(4-methylsulfonyl)phenyl-5-trifluoromethyl-pyridine;
2-(4-Chlorophenyl)-3-(4-methylsulfonyl)phenyl-5-trifluoromethyl-pyridine;

2-(4-Fluorophenyl)-3-(4-methylsulfonyl)phenyl-5-trifluoromethyl-pyridine;
3-(4-Methylsulfonyl)phenyl-2-(3-pyridinyl)-5-trifluoromethylpyridine;
5-Methyl-3-(4-methylsulfonyl)phenyl-2-phenylpyridine;
2-(4-Chlorophenyl)-5-methyl-3-(4-methylsulfonyl) phenylpyridine;
5-Methyl-3-(4-methylsulfonyl)phenyl-2-(3-pyridinyl) pyridine;
5-Chloro-2-(4-chlorophenyl)-3-(4-methylsulfonyl) phenylpyridine;
5-Chloro-3-(4-methylsulfonyl)phenyl-2-(2-pyridinyl) pyridine;
5-Chloro-3-(4-methylsulfonyl)phenyl-2-(3-pyridinyl) pyridine;
5-Chloro-3-(4-methylsulfonyl)phenyl-2-(4-pyridinyl) pyridine;
5-Chloro-3-(4-methylsulfonyl)phenyl-2-(2-methyl-5-pyridinyl)pyridine;
2-(4-Chlorophenyl)-3-(4-methylsulfonyl)phenylpyridinyl-5-carboxylic acid methyl ester;
2-(4-Chlorophenyl)-3-(4-methylsulfonyl)phenylpyridinyl-5-carboxylic acid;
5-Cyano-2-(4-chlorophenyl)-3-(4-methylsulfonyl) phenylpyridine;
5-Chloro-3-(4-methylsulfonyl)phenyl-2-(3-pyridyl)pyridine hydromethanesulfonate;
5-Chloro-3-(4-methylsulfonyl)phenyl-2-(3-pyridyl)pyridine hydrochloride;
5-Chloro-3-(4-methylsulfonyl)phenyl-2-(2-methyl-5-pyridinyl)pyridine Hydrochloride;
5-Chloro-3-(4-methylsulfonyl)phenyl-2-(2-ethyl-5-pyridinyl)pyridine; and
5-Chloro-3-(4-methylsulfonyl)phenyl-2-(2-ethyl-5-pyridinyl)pyridine hydromethanesulfonate.

Preferred compounds of formula I and Ic include those wherein $R^1$ is methyl or $NH_2$, especially methyl.

In another aspect the invention also encompasses a pharmaceutical composition for treating an inflammatory disease susceptable to treatment with an non-steroidal anti-inflammatory agent comprising:
a non-toxic therapeutically effective amount of a compound of formula I and a pharmaceutically acceptable carrier.

In another aspect the invention also encompasses a pharmaceutical composition for treating cyclooxygenase mediated diseases advantageously treated by an active agent that selectively inhibits COX-2 in preference to COX-1 comprising:
a non-toxic therapeutically effective amount of a compound of formula I and a pharmaceutically acceptable carrier.

In another aspect the invention also encompasses a method of treating an inflammatory disease susceptible to treatment with an non-steroidal anti-inflammatory agent comprising:
administration to a patient in need of such treatment of a non-toxic therapeutically effective amount of a compound of formula I and a pharmaceutically acceptable carrier.

In another aspect the invention also encompasses a method of treating cyclooxygenase mediated diseases advantageously treated by an active agent that selectively inhibits COX-2 in preference to COX-1 comprising:
administration to a patient in need of such treatment of a non-toxic therapeutically effective amount of a compound of formula I.

In another aspect the invention also encompasses the use of a compound of formula I or a pharmaceutical composition in the manufacture of a medicament for the treatment of an inflammatory disease susceptable to treatment with an a non-steroidal anti-inflammatory agent.

The invention is illustrated by Example 1 to 56.

The following abbreviations have the indicated meanings:
AA=arachidonic acid
Ac=acetyl
AIBN=2.2'-azobisisobutyronitrile
BHT=butylated hydroxytoluene
Bn=benzyl
CSA=camphor sulfonic acid (racemic)
dba=dibenzylideneacetone
DMAP=4-(dimethylamino)pyridine
DMF=N,N-dimethylformamide
DMSO=dimethyl sulfoxide
EDTA=ethylenediaminetetraacetic acid
ESA=ethane sulfonic acid
$Et_3N$=triethylamine
HBSS=Hanks balanced salt solution
HEPES=N-[2-Hydroxyethyl]piperazine-$N^1$-[2-ethanesulfonic acid]
HWB=human whole blood
KHMDS=potassium hexamethyldisilazane
LDA=lithium diisopropylamide
LPS=lipopolysaccharide
mCPBA=m-chloroperbenzoic acid
MMPP=magnesium monoperoxyphthalate
Ms=methanesulfonyl=mesyl
MsO=methanesulfonate=mesylate
MTBE=methyl tert-butyl ether
NBS=N-bromosuccinimide
NCS=N-chlorosuccinimide
NIS=N-iodosuccinimide
NMO=N-methylmorpholine-N-oxide
NMP=N-methylpyrrolidone
NSAID=non-steroidal anti-inflammatory drug
oxone®=$2KHSO_5 \cdot KHSO_4 \cdot K_2SO_4$
PCC=pyridinium chlorochromate
PDC=pyridinium dichromate
PEG=polyethyleneglycol
Ph=phenyl
pyr=pyridinyl
r.t.=room temperature
rac.=racemic
Tf=trifluoromethanesulfonyl=triflyl
TfO=trifluoromethanesulfonate=triflate
THF=tetrahydrofuran
TLC=thin layer chromatography
Ts=p-toluenesulfonyl=tosyl
TsO=p-toluenesulfonate=tosylate
Tz=1H (or 2H)-tetrazol-5-yl
$SO_2Me$=methyl sulfone
$SO_2NH_2$=sulfonamide
Alkyl group abbreviations
Me=methyl
Et=ethyl
n-Pr=normal propyl
i-Pr isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl c-Hex=cyclohexyl Dose Abbreviations bid=bis in die=twice daily qid=quater in die=four times a day tid=ter in die=three times a day For purposes of this specification alkyl is defined to include linear, branched and cyclic stuctures, with the indicated number of carbon atoms. Examples of alkyl are methyl, ethyl, propyl, s- and t-butyl, butyl, pentyl, hexyl, 1,1-dimethylethyl, cyclopropyl, cyclobutyl, cyclohexylmethyl and the like. Similarly, alkoxy and alkylthio mean linear, branched and cyclic stuctures, with the indicated number of carbon atoms.

For purposes of this specification fluoroalkyl means alkyl groups of the indicated number of carbon atoms in which one hydrogen or more is replaced by fluorine. Examples are —$CF_3$, —$CH_2CH_2F$, —$CH_2CF_3$, c-Pr-$F_5$, c-Hex-$F_{11}$ and the like. Similarly, fluoroalkoxy means linear, branched and cyclic stuctures, with the indicated number of carbon atoms.

For purposes of this specification, in situations in which a term occurs two or more times, the definition of the term in each occurrence is independent of the definition in each additional occurrence.

For purposes of this specification halo means F, Cl, Br, or I.

In another embodiment, the invention encompasses pharmaceutical compositions for inhibiting COX-2 and for treating COX-2 mediated diseases as disclosed herein comprising a pharmaceutically acceptable carrier and non-toxic therapeutically effective amount of a compound of formula I as described above.

In yet another embodiment, the invention encompasses a method of inhibiting cyclooxygenase and treating cyclooxygenase mediated diseases, advantageously treated by an active agent that selectively inhibits COX-2 in preference to COX-1 as disclosed herein comprising:

administration to a patient in need of such treatment of a non-toxic therapeutically effective amount of a compound of Formula I as disclosed herein.

Optical Isomers—Diastereomers—Geometric Isomers

Some of the compounds described herein contain one or more asymmetric centres and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, hydrabamine, N-(2-hydroxyethyl) piperidine, N-(2-hydroxyethyl)pyrrolidine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment which follows, references to the compounds of Formula I are meant to also include the pharmaceutically acceptable salts.

Utilities

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumour growth and hence can be used in the treatment of cancer. Compound 1 may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for treatment of glaucoma.

By virtue of its high inhibitory activity against COX-2 and/or its specificity for inhibiting COX-2 over COX-1, compound I will prove useful as an alternative to conventional NSAID'S, particularly where such non-steroidal anti-inflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anaemia such as hypoprothrombinemia, haemophilia or other bleeding problems; kidney disease; those prior to surgery or taking anticoagulants.

Pharmaceutical Compositions

For the treatment of any of these cyclooxygenase mediated diseases compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans. The compounds of the instant invention are particularly well suited for horses.

As indicated above, pharmaceutical compositions for treating COX-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, benzyl alcohol, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dose Ranges

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

Similarly, compound of Formula I, will be useful as a partial or complete substitute for conventional NSAID'S in preparations wherein they are presently co-administered with other agents or ingredients. Thus in further aspects, the invention encompasses pharmaceutical compositions for treating COX-2 mediated diseases as defined above comprising a non-toxic therapeutically effective amount of the compound of Formula I as defined above and one or more ingredients such as another pain reliever including acetaminophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a prostaglandin including misoprostol, enprostil, rioprostil, ornoprostol or rosaprostol: a diuretic; a sedating or non-sedating antihistamine. In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

Methods of Synthesis

The compounds of Formula I of the present invention can be prepared according to the synthetic routes outlined in Schemes 1 to 2 and by following the methods described therein.

SCHEME 1

The pyridines of Formula Ia and Ib may be prepared in a multi-step sequence from the requisite 2-aminopyridine II. Initial bromination of II with bromine in acetic acid provides the bromide III. A palladium-catalyzed coupling of III with 4-(methylthio)phenyl-boronic acid in the presence of a suitable base, such as sodium carbonate, provides the sulfide IV which can be oxidized using one of several oxidants, such as MMPP, oxone ®, or $OsO_4$/NMO to the corresponding sulfone V. The amino pyridine V can be converted to the halide VI via one of several methods. For example, treatment of V with sodium nitrite in the presence of HCl and bromine provides the bromide VI (X=Br). Alternatively, treatment of V with sodium nitrite and HCl followed by reaction with $POCl_3$ affords the corresponding chloride VI (X=Cl). A second palladium-catalyzed coupling of VI with an appropriately substituted metalated aromatic, such as an aryl boronic acid or an aryl stannane, provides the pyridine of Formula Ia. Suitable modification of the $R^2$ substituent in Ia provides additional examples of Ia. For example when $R^2$=Me, oxidation with an oxidant such as $KMnO_4$ provides the corresponding acid (Ia $R^2=CO_2H$) which can then be converted to the methyl ester (Ia $R^2=CO_2Me$), using a reagent such as diazomethane. Alternatively, treatment of the acid with chlorosulfonylisocyanate and DMF provides the nitrile (Ia $R^2=CN$). The pyridine methyl sulfones Ia can be converted to the corresponding pyridine sulfonamides Ib by using procedures described in the literature (Huang et. al. Tetrahedron Lett. 1994, 39, 7201).

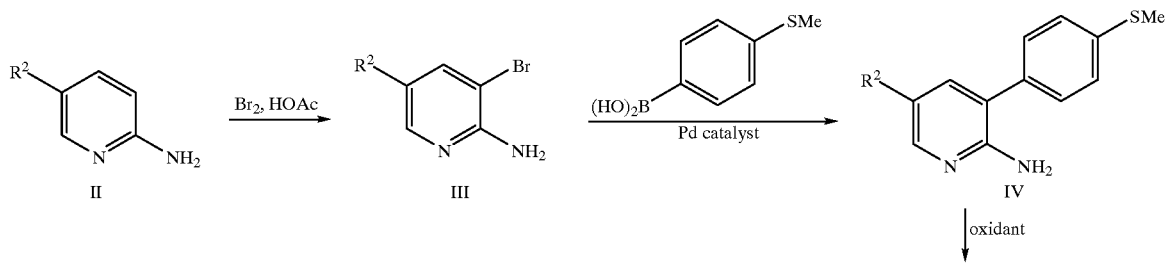

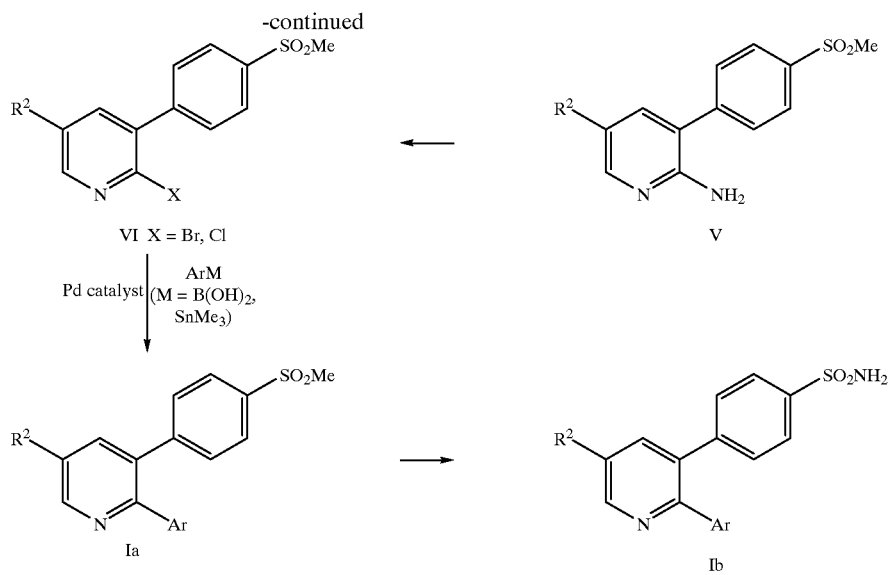

SCHEME 2

The 2-halopyridines VI of Scheme 1 can also be prepared in a multi-step process from the appropriate 2-hydroxypyridines VII. First, treatment of VII with bromine in acetic acid provides the bromide VIII. Subsequent reaction of VIII with benzyl bromide in the presence of a base such as silver carbonate yields the benzyl ether IX which can be converted to the sulfone X via a sequence of reactions similar to those described for the conversion of bromide III to V in Scheme 1. The benzyl protecting group can be removed by treatment of IX with an acid such as trifluoroacetic acid to afford the hydroxypyridine X. Heating X with POBr$_3$ or POCl$_3$ provides the corresponding 2-halopyridines VI (X=Br, Cl) of Scheme 1.

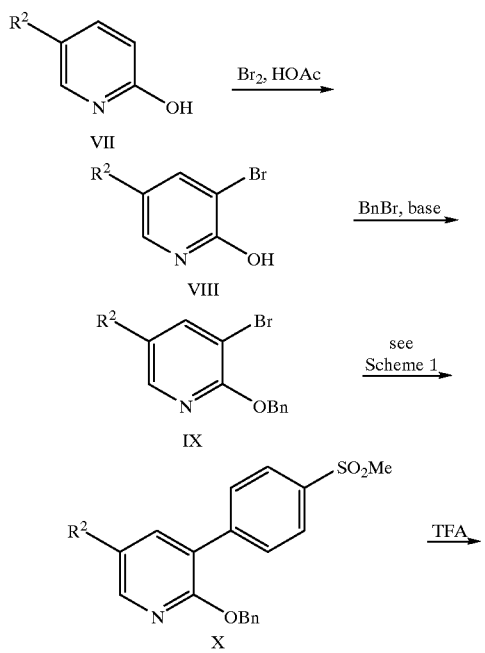

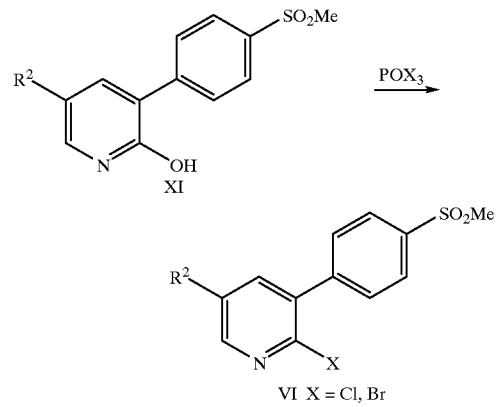

REPRESENTATIVE COMPOUNDS

Tables 1 and 2 illustrate compounds of formula Ia and Ib, which are representative of the present invention.

TABLE 1

Ia

| Ex. | R² | Ar |
|---|---|---|
| 1 | CF$_3$ | Ph |
| 2 | CF$_3$ | 3-ClC$_6$H$_4$ |
| 3 | CF$_3$ | 4-ClC$_6$H$_4$ |
| 4 | CF$_3$ | 4-FC$_6$H$_4$ |
| 5 | CF$_3$ | 2-(CMe$_2$OH)C$_6$H$_4$ |
| 6 | CF$_3$ | 3-(CMe$_2$OH)C$_6$H$_4$ |
| 7 | CF$_3$ | 3-pyr |
| 8 | CF$_3$ | 5-(2-Me)pyr |

TABLE 1-continued

Ia: structure with R² on pyridine (position 5), Ar on pyridine (position 2), and 4-(SO₂Me)phenyl on pyridine (position 3).

| Ex. | R² | Ar |
|---|---|---|
| 9 | CF₃ | 5-(3-Br)pyr |
| 10 | CF₃ | 5-(3-Cl)pyr |
| 11 | CF₃ | 5-(2-OMe)pyr |
| 12 | CF₃ | 2-(5-Br)pyr |
| 13 | Me | Ph |
| 14 | Me | 4-ClC₆H₄ |
| 15 | Me | 3-pyr |
| 16 | Cl | Ph |
| 17 | Cl | 4-ClC₆H₄ |
| 18 | Cl | 2-(CMe₂OH)C₆H₄ |
| 19 | Cl | 3-(CMe₂OH)C₆H₄ |
| 20 | Cl | 2-pyr |
| 21 | Cl | 3-pyr |
| 22 | Cl | 4-pyr |
| 23 | Cl | 5-(2-Me)pyr |
| 24 | Cl | 5-(3-Br)pyr |
| 25 | Cl | 5-(3-Cl)pyr |
| 26 | Cl | 5-(2-OMe)pyr |
| 27 | Cl | 2-(5-Br)pyr |
| 28 | F | Ph |
| 29 | F | 3-pyr |
| 30 | F | 5-(2-Me)pyr |
| 31 | Br | Ph |
| 32 | Br | 3-pyr |
| 33 | Br | 5-(2-Me)pyr |
| 34 | NO₂ | Ph |
| 35 | NO₂ | 3-pyr |
| 36 | NO₂ | 5-(2-Me)pyr |
| 37 | OMe | Ph |
| 38 | OMe | 3-pyr |
| 39 | OMe | 5-(2-Me)pyr |
| 40 | NHCOMe | Ph |
| 41 | NHCOMe | 3-pyr |
| 42 | NHCOMe | 5-(2-Me)pyr |
| 43 | CO₂Me | 4-ClC₆H₄ |
| 44 | CO₂H | 4-ClC₆H₄ |
| 45 | CN | 4-ClC₆H₄ |
| 46 | Cl | 3-pyr.MeSO₃H |
| 47 | Cl | 3-pyr.HCl |
| 57 | Cl | 3-pyr.CSA |
| 58 | Cl | 3-pyr.ESA |
| 59 | Cl | 5-(2-Me)pyr.HCl |
| 60 | Cl | 5-(2-CH₂OH)pyr |
| 61 | Cl | 5-(2-CO₂H)pyr |
| 62 | Cl | 5-(2-Me)pyr-N-oxide |
| 63 | Cl | 5-(3-Me)pyr |
| 64 | Cl | 3-(4-Me)pyr |
| 65 | Cl | 3-(2-Me)pyr |
| 66 | Cl | 3-(2-Et)pyr |
| 67 | Cl | 3-(2-c-Pr)pyr |
| 68 | Me | 3-pyr.HCl |
| 69 | CN | 3-pyr |
| 70 | CN | 5-(2-Me)pyr |
| 71 | Cl | 5-(2-Et)pyr |
| 72 | Cl | 5-(2-Et)pyr-MeSO₃H |
| 73 | Cl | 5-(2-c-Pr)pyr |
| 74 | Cl | 3-(2,6-Me₂)pyr |

TABLE 2

Ib: structure with R² on pyridine (position 5), Ar on pyridine (position 2), and 4-(SO₂NH₂)phenyl on pyridine (position 3).

| Ex. | R² | Ar |
|---|---|---|
| 48 | CF₃ | Ph |
| 49 | CF₃ | 4-ClC₆H₄ |
| 50 | CF₃ | 4-FC₆H₄ |
| 51 | CF₃ | 3-pyr |
| 52 | Me | Ph |
| 53 | Me | 4-ClC₆H₄ |
| 54 | Cl | 3-pyr |
| 55 | Cl | 5-(2-Me)pyr |
| 56 | CN | 4-ClC₆H₄ |

ASSAYS FOR DETERMINING BIOLOGICAL ACTIVITY

The compound of Formula I can be tested using the following assays to determine their COX-2 inhibiting activity.

INHIBITION OF CYCLOOXYGENASE ACTIVITY

Compounds are tested as inhibitors of cyclooxygenase activity in whole cell cyclooxygenase assays. Both of these assays measure prostaglandin $E_2$ synthesis in response to AA, using a radioimmunoassay. Cells used for these assays are human osteosarcoma 143 cells (which specifically express COX-2) and human U-937 cells (which specifically express COX-1). In these assays, 100% activity is defined as the difference between prostaglandin $E_2$ synthesis in the absence and presence of arachidonate.

Whole Cell Assays

For cyclooxygenase assays, osteosarcoma cells are cultured in 1 mL of media in 24-well multidishes (Nunclon) until confluent (1–2×10⁵ cells/well). U-937 cells are grown in spinner flasks and resuspended to a final density of 1.5×10⁶ cells/mL in 24-well multidishes (Nunclon). Following washing and resuspension of osteosarcoma and U-937 cells in 1 mL of HBSS, 1 μL of a DMSO solution of test compound or DMSO vehicle is added, and samples gently mixed. All assays are performed in triplicate. Samples are then incubated for 5 or 15 minutes at 37° C., prior to the addition of AA. AA (peroxide-free, Cayman Chemical) is prepared as a 10 mM stock solution in ethanol and further diluted 10-fold in HBSS. An aliquot of 10 μL of this diluted solution is added to the cells to give a final AA concentration of 10 μM. Control samples are incubated with ethanol vehicle instead of AA. Samples are again gently mixed and incubated for a further 10 min. at 37° C. For osteosarcoma cells, reactions are then stopped by the addition of 100 μL of 1 N HCl, with mixing and by the rapid removal of the solution from cell monolayers. For U-937 cells, reactions are stopped by the addition of 100 μL of 1 N HCl, with mixing. Samples are then neutralized by the addition of 100 μL of 1 N NaOH and $PGE_2$ levels measured by radioimmunoassay.

Whole Cell Assays for COX-2 and COX-1 using CHO Transfected Cell Lines

Chinese hamster ovary (CHO) cell lines which have been stably transfected with an eukaryotic expression vector pCDNAIII containing either the human COX-1 or COX-2 cDNA's are used for the assay. These cell lines are referred to as CHO [hCOX-1] and CHO [hCOX-2], respectively. For cyclooxygenase assays, CHO[hCOX-1] cells from suspension cultures and CHO[hCOX-2] cells prepared by trypsinization of adherent cultures are harvested by centrifugation (300×g, 10 min) and washed once in HBSS containing 15 mM HEPES, pH 7.4, and resuspended in HBSS, 15 mM HEPES, pH 7.4, at a cell concentration of $1.5 \times 10^6$ cells/ml. Drugs to be tested are dissolved in DMSO to 66.7-fold the highest test drug concentration. Compounds are typically tested at 8 concentrations in duplicate using serial 3-fold serial dilutions in DMSO of the highest drug concentration. Cells ($0.3 \times 10^6$ cells in 200 $\mu$l) are preincubated with 3 $\mu$l of the test drug or DMSO vehicle for 15 min at 37° C. Working solutions of peroxide-free AA (5.5 $\mu$M and 110 $\mu$M AA for the CHO [hCOX-1] and CHO [COX-2] assays, respectively) are prepared by a 10-fold dilution of a concentrated AA solution in ethanol into HBSS containing 15 mM HEPES, pH 7.4. Cells are then challenged in the presence or absence of drug with the AA/HBSS solution to yield a final concentration of 0.5 $\mu$M AA in the CHO[hCOX-1] assay and a final concentration of 10 $\mu$M AA in the CHO[hCOX-2] assay. The reaction is terminated by the addition of 10 $\mu$l 1 N HCl followed by neutralization with 20 $\mu$l of 0.5 N NaOH. The samples are centrifuged at 300×g at 4° C. for 10 min, and an aliquot of the clarified supernatant is appropriately diluted for the determination of $PGE_2$ levels using an enzyme-linked immunoassay for $PGE_2$ (Correlate $PGE_2$ enzyme immunoassay kit, Assay Designs, Inc.). Cyclooxygenase activity in the absence of test compounds is determined as the difference in $PGE_2$ levels of cells challenged with AA versus the $PGE_2$ levels in cells mock-challenged with ethanol vehicle. Inhibition of $PGE_2$ synthesis by test compounds is calculated as a percentage of the activity in the presence of drug versus the activity in the positive control samples.

Assay of COX-1 Activity from U937 Cell Microsomes

U 937 cells are pelleted by centrifugation at 500×g for 5 min and washed once with phosphate-buffered saline and repelleted. Cells are resuspended in homogenization buffer consisting of 0.1 M Tris-HCl, pH 7.4, 10 mM EDTA, 2 $\mu$g/ml leupeptin, 2 $\mu$g/ml soybean trypsin inhibitor, 2 $\mu$g/ml aprotinin and 1 mM phenyl methyl sulfonyl fluoride. The cell suspension is sonicated 4 times for 10 sec and is centrifuged at 10,000×g for 10 min at 4° C. The supernatant is centrifuged at 100,000×g for 1 hr at 4° C. The 100,000×g microsomal pellet is resuspended in 0.1 M Tris-HCl, pH 7.4, 10 mM EDTA to approximately 7 mg protein/ml and stored at –80° C.

Microsomal preparations are thawed immediately prior to use, subjected to a brief sonication, and then diluted to a protein concentration of 125 $\mu$g/ml in 0.1 M Tris-HCl buffer, pH 7.4 containing 10 mM EDTA, 0.5 mM phenol, 1 mM reduced glutathione and 1 $\mu$M hematin. Assays are performed in duplicate in a final volume of 250 $\mu$l. Initially, 5 $\mu$l of DMSO vehicle or drug in DMSO are added to 20 $\mu$l of 0.1 M Tris-HCl buffer, pH 7.4 containing 10 mM EDTA in wells of a 96-deepwell polypropylene titre plate. 200 $\mu$l of the microsomal preparation are then added and pre-incubated for 15 min at room temperature before addition of 25 $\mu$l of 1 M arachidonic acid in 0.1 M Tris-HCl and 10 mM EDTA, pH 7.4. Samples are incubated for 40 min at room temperature and the reaction is stopped by the addition of 25 $\mu$l of 1 N HCl. Samples are neutralized with 25 $\mu$l of 1 N NaOH prior to quantitation of $PGE_2$ content by radioimmunoassay (Dupont-NEN or Amersham assay kits). Cyclooxygenase activity is defined as the difference between $PGE_2$ levels in samples incubated in the presence of arachidonic acid and ethanol vehicle.

Assay of the Activity of Purified Human COX-2

The enzyme activity is measured using a chromogenic assay based on the oxidation of N,N,N',N'-tetramethyl-p-phenylenediamine (TMPD) during the reduction of $PGG_2$ to $PGH_2$ by COX-2 (Copeland et al. (1994) Proc. Natl. Acad. Sci. 91, 11202–11206).

Recombinant human COX-2 is purified from Sf9 cells as previously described (Percival et al (1994) Arch. Biochem. Biophys. 15, 111–118). The assay mixture (180 $\mu$L) contains 100 mM sodium phosphate, pH 6.5, 2 mM genapol X-100, 1 $\mu$M hematin, 1 mg/ml gelatin, 80–100 units of purified enzyme (One unit of enzyme is defined as the amount of enzyme required to produce an O.D. change of 0.001/min at 610 nm) and 4 $\mu$L of the test compound in DMSO. The mixture is pre-incubated at room temperature (22° C.) for 15 minutes prior to initiation of the enzymatic reaction by the addition of 20 $\mu$L of a sonicated solution of 1 mM AA and 1 mM TMPD in assay buffer (without enzyme or hematin). The enzymatic activity is measured by estimation of the initial velocity of TMPD oxidation over the first 36 sec of the reaction. A non-specific rate of oxidation is observed in the absence of enzyme (0.007–0.010 O.D./min) and is subtracted before the calculation of the % inhibition. $IC_{50}$ values are derived from 4-parameter least squares non-linear regression analysis of the log-dose vs % inhibition plot.

HUMAN WHOLE BLOOD ASSAY

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on $PGE_2$ production. As well, platelets in whole blood contain a large amount of the COX-1 enzyme. Immediately following blood clotting, platelets are activated through a thrombin-mediated mechanism. This reaction results in the production of thromboxane $B_2$ ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

METHOD

Step A: COX-2 (LPS-induced $PGE_2$ Production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2 mL blood aliquot to use as blank (basal levels of $PGE_2$). The remaining blood is incubated with LPS (100 $\mu$g/ml final concentration, Sigma Chem, #L-2630 from *E. coli;* diluted in 0.1% BSA (Phosphate buffered saline) for 5 minutes at room temperature. Five hundred $\mu$L aliquots of blood are incubated with either 2 μL of vehicle (DMSO) or 2 μL of a test compound at final concentrations varying from 10 nM to 30 μM for 24 hours at 37° C. At the end of the incubation, the blood is centrifuged at 12,000×g for 5 minutes to obtain plasma. A 100 μL aliquot of plasma is mixed with 400 μL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

Step B: COX-1 (Clotting-induced $TxB_2$ Production)

Fresh blood is collected into vacutainers containing no anticoagulants. Aliquots of 500 μL are immediately transferred to siliconized microcentrifuge tubes preloaded with 2 μL of either DMSO or a test compound at final concentrations varying from 10 nM to 30 μM. The tubes are vortexed and incubated at 37° C. for 1 hour to allow blood to clot. At the end of incubation, serum is obtained by centrifugation (12,000×g for 5 min.). A 100 μL aliquot of serum is mixed with 400 μL of methanol for protein precipitation. The supernatant is obtained and is assayed for $TxB_2$ using a enzyme immunoassay kit (Cayman, #519031) according to the manufacturer's instruction.

RAT PAW EDEMA ASSAY

Protocol

Male Sprague-Dawley rats (150–200 g) are fasted overnight and are given, po, either vehicle (1% methocel or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 μl of 1% carrageenan solution in saline (FMC Corp, Maine) into the paw using an insulin syringe with a 25-gauge needle (i.e. 500 μg carrageenan per paw). Three hr later, the paw volume ($V_3$) is measured and the increases in paw volume ($V_3-V_0$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

NSAID-INDUCED GASTROPATHY IN RATS

Rationale

The major side effect of conventional NSAIDs is their ability to produce gastric lesions in man. This action is believed to be caused by inhibition of COX-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}$Cr excretion after systemic injection of $^{51}$Cr-labeled red blood cells. Fecal $^{51}$Cr excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}$Cr-labeled red blood cells from a donor rat. The animals are placed individually in metabolism cages with food and water ad lib. Feces are collected for a 48 h period and $^{51}$Cr fecal excretion is calculated as a percent of total injected dose. $^{51}$Cr-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400μ Ci of sodium [51]chromate for 30 min. at 37° C. At the end of the incubation, the red blood cells are washed twice with 20 mL HBSS to remove free sodium [51]chromate. The red blood cells are finally reconstituted in 10 mL HBSS and 0.5 mL of the solution (about 20μ Ci) is injected per rat.

PROTEIN-LOSING GASTROPATHY IN SQUIRREL MONKEYS

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of [51]$CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous [51]Cr (5μ Ci/kg in 1 ml/kg phosphate buffer saline (PBS)) is administered 1 h after the last drug/vehicle dose, and feces collected for 24 h in a metabolism cage and assessed for excreted $^{51}$Cr by gamma-counting. Venous blood is sampled 1 h and 8 h after the last drug dose, and plasma concentrations of drug measured by RP-HPLC.

LPS-Induced Pyrexia in Conscious Rats

Male Sprague-Dawley rats (150–200 g) were fasted for 16–18 h before use. At approximately 9:30 a.m., the animals were placed temporarily in plexiglass restrainers and their baseline rectal temperature was recorded using a flexible temperature probe (YSI series 400) connected to a digital thermometer (Model 08502, Cole Parmer). The same probe and thermometer were used for all animals to reduce experimental error. The animals were returned to their cages after the temperature measurements. At time zero, the rats were injected intraperitoneally with either saline or LPS (2 mg/kg, Sigma Chem) and the rectal temperature was remeasured at 5, 6 and 7 h following LPS injection. After the measurement at 5 h, when the increase in temperature had reached a plateau, the LPS-injected rats were given either the vehicle (1% methocel) or a test compound orally to determine whether the compound could reverse the pyrexia. Percent reversal of the pyrexia was calculated using the rectal temperature obtained at 7 h in the control (vehicle-treated) group as the reference (zero reversal) point. Complete reversal of pyrexia to the pre-LPS baseline value is taken as 100%.

LPS-Induced Pyrexia in Conscious Squirrel Monkeys

Temperature probes were surgically implanted under the abdominal skin in a group of squirrel monkeys (*Saimiri sciureus*) (1.0–1.7 kg). This allows for the monitoring of body temperature in conscious, unrestrained monkeys by a telemetric sensing system (Data Sciences International, Minnesota). The animals were fasted and were placed in individual cages for acclimatization 13–14 h before use. Electronic receivers were installed on the side of the cages which pick up signals from the implanted temperature probes. At approximately 9:00 a.m. on the day of the experiment, the monkeys were restrained temporarily in training chairs and were given a bolus I.V. injection of LPS, (6 mg/kg, dissolved in sterile saline). The animals were returned to their cages and body temperature was recorded continuously every 5 min. Two h after injection of LPS, when the body temperature had increased by 1.5–2 C, the monkeys were dosed orally with either vehicle (1% methocel) or a test compound (3 mg/kg). One hundred minutes later, the difference between the body temperature and the baseline value was determined. Percent inhibition was calculated taking the value in the control group as 0% inhibition.

Acute Inflammatory Hyperalgesia Induced by Carrageenan in Rats

Experiments were performed using male Sprague Dawley rats (90–100 g). Hyperalgesia to mechanical compression of the hind paw was induced by intraplantar injection of carrageenan (4.5 mg into one hind paw) 3 h previously. Control animals received an equivalent volume of saline (0.15 ml intraplantar). A test compound (0.3–30 mg/kg, suspended in 0.5% methocel in distilled water) or vehicle (0.5% methocel) was administered orally (2 ml/kg) 2 h after carrageenan. The vocalisation response to compression of the hind paw was measured 1 h later using a Ugo Basile algesiometer.

Statistical analysis for carrageenan-induced hyperalgesia was performed using one-way ANOVA (BMDP Statistical Software Inc.). Hyperalgesia was determined by subtracting the vocalisation threshold in saline injected rats from that obtained in animals injected with carrageenan. Hyperalgesia scores for drug-treated rats were expressed as a percentage of this response. $ID_{50}$ values (the dose producing 50% of the maximum observed response) were then calculated by non-linear least squares regression analysis of mean data using GraFit (Erithacus Software).

Adjuvant-Induced Arthritis in Rats

Seventy, 6.5–7.5 week old, female Lewis rats (body weight ~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of *Mycobacterium butyricum* in 0.1 ml of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day-1) and 21 days following adjuvant injection, and primary paw volumes were determined before (day-1) and on days 4 and 21 following adjuvant injection. The rats were anesthetized with an intramuscular injection of 0.03–0.1 ml of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subchondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0.1, 0.3, 1, and 3 mg/kg/day, Indomethacin at a total daily dose of 1 mg/kg/day, or vehicle (0.5% methocel in sterile water) were administered per os b.i.d. beginning post injection of adjuvant and continuing for 21 days. The compounds were prepared weekly, refrigerated in the dark until used, and vortex mixed immediately prior to administration.

Two-factor ('treatment' and 'time') analysis of variance with repeated measures on 'time' were applied to the % changes for body weight and foot volumes and to the rank-transformed radiographic total scores. A post hoc Dunnett's test was conducted to compare the effect of treatments to vehicle. A one-way analysis of variance was applied to the thymic and spleen weights followed by the Dunnett's test to compare the effect of treatments to vehicle. Dose-response curves for % inhibition in foot volumes on days 4, 14 and 21 were fitted by a 4-parameter logistic function using a non-linear least squares' regression. $ID_{50}$ was defined as the dose corresponding to a 50% reduction from the vehicle and was derived by interpolation from the fitted 4-parameter equation.

PHARMACOKINETICS IN RATS

Per Os Pharmacokinetics in Rats

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.

Vehicles

The following vehicles may be used in PO rat blood level determinations:

| | |
|---|---|
| PEG 200/300/400 | restricted to 2 mL/kg |
| Methocel 0.5%–1.0% | 10 mL/kg |
| Tween 80 | 10 mL/kg |

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h·kg (milliliters per hour kilogram)

Intravenous Pharmacokinetics in Rats

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles

The following vehicles may be used in IV rat blood level determinations:

| | |
|---|---|
| Dextrose | 1 mL/kg |
| Moleculosol 25% | 1 mL/kg |
| DMSO (dimethylsulfoxide) | Restricted to a dose volume of 0.1 mL per animal |
| PEG 200 | Not more than 60% mixed with 40% sterile water-1 mL/kg |

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h·kg (milliliters per hour kilogram)

REPRESENTATIVE BIOLOGICAL DATA

Compounds of the present invention are inhibitors of COX-2 and are thereby useful in the treatment of COX-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of AA, COX-1 or COX-2 and a putative inhibitor. The $IC_{50}$ values represent the concentration of putative inhibitor required to lower $PGE_2$ synthesis to 50% of that obtained as compared to the uninhibited control.

Data from three of these biological assays is given for representative compounds along with comparative data for the following two compounds from World Patent Application 96/10012:

TABLE 3

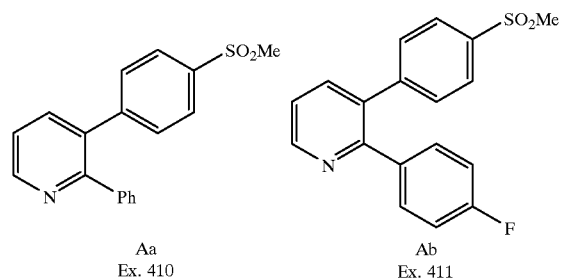

Aa
Ex. 410

Ab
Ex. 411

| Example | Cox-2 Whole Blood ($IC_{50}$, μM) | Cox-1 U937 ($IC_{50}$, μM) | Selectivity Ratio | Rat Paw Edema ($ED_{50}$, mg/kg) |
|---|---|---|---|---|
| Aa | 7.9 | >10 | >1.3 | >10 |
| Ab | 4.9 | 2.2 | 0.45 | — |

TABLE 3-continued

Aa Ex. 410: pyridine with 4-(SO2Me)phenyl and Ph substituents

Ab Ex. 411: pyridine with 4-(SO2Me)phenyl and 4-F-phenyl substituents

| Example | Cox-2 Whole Blood (IC$_{50}$, μM) | Cox-1 U937 (IC$_{50}$, μM) | Selectivity Ratio | Rat Paw Edema (ED$_{50}$, mg/kg) |
|---|---|---|---|---|
| 1 | 0.3 | 1.5 | 4.4 | 5.4 |
| 3 | 0.9 | 1.8 | 2 | — |
| 4 | 0.3 | 1 | 3.3 | — |
| 7 | 1.8 | 5 | 2.8 | 1.7 |
| 13 | 0.5 | 3 | 6 | — |
| 14 | 0.7 | 1.4 | 2 | — |
| 21 | 1.0 | 16 | 16 | 2.3 |
| 23 | 1.1 | >10 | >9.1 | 0.6 |
| 32 | 1.2 | >10 | >8.3 | 0.9 |
| 45 | 2.2 | >10 | >4.5 | 3.0 |
| 46 | | | | 3.3 |
| 47 | | | | 2.4 |
| 59 | | | | 0.8 |
| 71 | 1.7 | >10 | >5.8 | 1.6 |
| 73 | 1.8 | 7 | 3.8 | 2.0 |

As can be seen from this data, the compounds of the present invention show greater COX-2 selectivity and potency than Aa and Ab. Moreover, the basicity of the pyridine ring in these examples permits the formation of acid salts, resulting in increased water solubility and gives the potential for parenteral administration in aqueous vehicles.

The invention will now be illustrated by the following non-limiting examples in which, unless stated otherwise:

(i) all operations were carried out at room or ambient temperature, that is, at a temperature in the range 18–25° C. and drying of organics was done using MgSO$_4$, (ii) evaporation of solvent was carried out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)), r.t. (room temperature).

EXAMPLE 1

3-(4-Methylsulfonyl)phenyl-2-phenyl-5-trifluoromethylpyridine

Step 1: 2-Amino-3-bromo-5-trifluoromethylpyridine

To a solution of 2-amino-5-trifluoromethylpyridine (9 g) in acetic acid (75 mL) at r.t. was added bromine (5.8 mL) slowly. After 1 h, the acid was neutralized by the careful addition of sodium hydroxide (10 N) at 0° C. The resulting orange precipitate was dissolved in ether and washed successively with saturated potassium carbonate, saturated Na$_2$SO$_3$ and brine, dried and concentrated. The residual solid was stirred vigorously in hexane for 1 h to provide, after filtration, the title compound as a white solid (10.2 g).

Step 2: 2-Amino-3-(4-methylthio)phenyl-5-trifluoromethylpyridine

A mixture of the bromide from Step 1, 4-methylthiobenzene boronic acid (Li, et. al. *J. Med. Chem.* 1995, 38, 4570) (8.5 g), 2 M aqueous sodium carbonate (60 mL) and palladium tetrakis(triphenylphosphine) (490 mg) in ethanol/benzene (100 mL, 1:1) was heated at reflux for 15 h. The mixture was cooled to r.t., diluted with water and extracted with ether. The organics were concentrated and the residue was subjected to stirred vigorously in ether/hexane for 1 h to provide, after filtration, the title compound (11.2 g) as a beige solid.

Step 3: 2-Amino-3-(4-methylsulfonyl)phenyl-5-trifluoromethylpyridine

A mixture of 2-amino-3-(4-methylthio)phenyl-5-trifluoromethylpyridine (9.7 g), OsO$_4$ (2 mL of a 4% solution in water) and NMO (13 g) in acetone/water (60 mL:5 mL) was stirred at r.t. overnight. Saturated aqueous Na$_2$SO$_3$ was then added and the resulting mixture was stirred for 30 min. The acetone was evaporated and the resulting mixture was extracted with ether and ethyl acetate. The combined organics were washed with Na$_2$SO$_3$, water, brine and then concentrated. The solid residue was stirred vigorously in hexane and ether for 1 h and then filtered to provide the title compound as a pale yellow solid (9.9 g).

Step 4: 2-Chloro-3-(4-methylsulfonyl)phenyl-5-trifluoromethylpyridine

To a solution of 2-amino-3-(4-methylsulfonyl)phenyl-5-trifluoromethylpyridine (1.2 g) in water/concentrated HCl (9.5 mL:1 mL) at 0° C. was added a solution of sodium nitrite (262 mg) in 5 mL water. The mixture was warmed to r.t. and stirred overnight. An additional 30 mg of sodium nitrite was added and after 3 h the heterogeneous mixture was filtered. A portion of the solid (250 mg) and POCl$_3$ (110 μL) in DMF (2 mL) was heated at 70° C. for 60 h. The mixture was cooled to r.t., diluted with water and extracted with ethyl acetate. The organics were washed with brine, dried and concentrated to provide the title compound as a pale yellow solid (270 mg) that was used as such in the subsequent reaction.

Step 5: 3-(4-Methylsulfonyl)phenyl-2-phenyl-5-trifluoromethylpyridine

A mixture of 2-chloro-3-(4-methylsulfonyl)phenyl-5-trifluoromethylpyridine (260 mg), benzene boronic acid (113 mg), 2 M aqueous sodium carbonate (2.1 mL) and palladium tetrakis(triphenylphosphine) (30 mg) in ethanol/benzene (8 mL, 1:1) was heated at reflux for 24 h. The mixture was cooled to r.t., diluted with water and extracted with ethyl acetate. The organics were concentrated and the solid residue was subjected to flash chromatography (eluting with hexane/ethyl acetate, 4:1 v/v) to provide the title compound as a white solid, m.p. 191–192° C. (215 mg).

EXAMPLE 2

2-(3-Chlorophenyl)-3-(4-methylsulfonyl)phenyl-5-trifluoromethylpyridine

Step 1: 2-Bromo-3-(4-methylsulfonyl)phenyl-5-trifluoromethylpyridine

To a solution of 2-amino-3-(4-methylsulfonyl)phenyl-5-trifluoromethylpyridine from Example 1, Step 3 (2 g) in 48% HBr (25 mL) at 0° C. was added bromine (3 mL) and then sodium nitrite. (1.1 g) portionwise. After 2 h, the solution was neutralized by the addition of sodium hydroxide (10 N) and then extracted with ethyl acetate. The organics were washed with saturated $Na_2SO_3$ and brine, dried and concentrated. Flash chromatography of the residual material (eluting with hexane/ethyl acetate, 7:3 to 3:7 v/v) provided the title compound as a white solid (435 mg).

Step 2: 2-(3-Chlorophenyl)-3-(4-methylsulfonyl)phenyl-5-trifluoromethylpyridine

A mixture of 2-bromo-3-(4-methylsulfonyl)phenyl-5-trifluoromethylpyridine (178 mg), 3-chlorophenyl boronic acid (110 mg), potassium phosphate (225 mg) and palladium tetrakis(triphenylphosphine) (20 mg) in dioxane (10 mL) was heated at reflux for 24 h. After cooling to room temperature, the mixture was diluted with water and extracted with ether. The organics were dried and concentrated and the residual material was subjected to flash chromatography (eluting with hexane/ethyl acetate, 7:3 v/v). The solid that was obtained was stirred vigorously in hexane/ether for 1 h to provide the title compound as a pale yellow solid, m.p. 136–237° C. (115 mg).

EXAMPLE 3

2-(4-Chlorophenyl)-3-(4-methylsulfonyl)phenyl-5-trifluoromethylpyridine

Following the procedures described in Example 1, Step 5, but substituting 4-chlorophenyl boronic acid for benzene boronic acid, the title compound was obtained as a white solid, m.p. 192–193° C. (155 mg).

EXAMPLE 4

2-(4-Fluorophenyl)-3-(4-methylsulfonyl)phenyl-5-trifluoromethylpyridine

Following the procedures described in Example 1, Step 5, but substituting 4-fluorophenyl boronic acid for benzene boronic acid, the title compound was obtained as a white solid, m.p. 163–164° C. (152 mg).

EXAMPLE 7

3-(4-Methylsulfonyl)phenyl-2-(3-pyridinyl)-5-trifluoromethylpyridine

A mixture of 2-bromo-3-(4-methylsulfonyl)phenyl-5-trifluoromethylpyridine (600 mg) (Example 2, Step 2), diethyl-3-pyridinylborane (255 mg), sodium carbonate (2 M, 2.2 mL) and bis(triphenylphosphine)palladium dibromide (25 mg) in benzene/ethanol (1:1, 32 mL) was heated at reflux for 24 h. After cooling to r.t., the mixture was concentrated, diluted with water and extracted with ethyl acetate. The organics were concentrated and the residual material was dissolved in 10% HCl/ether. The organic phase was removed and the aqueous phase was adjusted to ~pH 10 by the addition of saturated sodium bicarbonate. The mixture was extacted with ethyl acetate and the combined organics were concentrated and subjected to flash chromatography (eluting with ethyl acetate) to provide the title compound as a white solid, m.p. 171–172° C. (180 mg).

EXAMPLE 13

5-Methyl-3-(4-methylsulfonyl)phenyl-2-phenylpyridine

Step 1: 2-Amino-3-bromo-5-methylpyridine

To a solution of 2-amino-5-picoline (5 g) in acetic acid (40 mL) at r.t. was added bromine (2.6 mL) slowly. After 1 h, the acid was neutralized by the careful addition of sodium hydroxide (10 N) at 0° C. The resulting orange precipitate was dissolved in ether and washed successively with saturated potassium carbonate, saturated $Na_2S_2O_3$ and brine, dried and concentrated. Flash chromatography (eluting with hexane/ethyl acetate, 3:2 v/v) of the residual solid provided the title compound as a pale yellow solid (7.1 g).

Step 2: 2-Amino-5-methyl-3-(4-methylsulfonyl)phenylpyridine

Following the procedures described in Example 1, Steps 2 and 3, but substituting 2-amino-3-bromo-5-methylpyridine (7.1 g) from Step 1 for 2-amino-3-bromo-5-trifluoromethylpyridine, the title compound was obtained as a pale yellow solid (3.7 g).

Step 3: 2-Bromo-5-methyl-3-(4-methylsulfonyl)phenylpyridine

Following the procedures described in Example 2, Step 1, but substituting 2-amino-5-methyl-3-(4-methylsulfonyl)phenyl-pyridine (3 g) from Step 2 for 2-amino-3-(4-methylsulfonyl)phenyl-5-trifluoromethylpyridine, the title compound was obtained as a white solid (2.7 g).

Step 4: 5-Methyl-3-(4-methylsulfonyl)phenyl-2-phenylpyridine

Following the procedures described in Example 1, Step 5, but substituting 2-bromo-5-methyl-3-(4-methylsulfonyl)phenylpyridine (300 mg) from Step 3 for 2-chloro-3-(4-methylsulfonyl)phenyl-5-trifluoromethylpyridine, the title compound was obtained as a pale yellow solid (270 mg). $^1$H NMR (300 MHz, $CDCl_3$) δ 2.42 (s, 3H), 3.03 (s, 3H), 7.19–7.28 (m, 5H), 7.35 (d, 2H), 7.51 (d, 1H), 7.81 (d, 2H), 8.56 (d, 1H).

EXAMPLE 14

2-(4-Chlorophenyl)-5-methyl-3-(4-methylsulfonyl)phenylpyridine

Following the procedures described in Example 3, but substituting 2-bromo-5-methyl-3-(4-methylsulfonyl)phenylpyridine (300 mg) from Example 13, Step 3 for 2-chloro-3-(4-methylsulfonyl)phenyl-5-trifluoromethylpyridine, the title compound was obtained as a white solid, m.p. 155–156° C. (125 mg).

EXAMPLE 15

5-Methyl-3-(4-methylsulfonyl)phenyl-2-(3-pyridinyl)pyridine

Step 1: Lithium Tri-n-propoxy-3-pyridinylboronate

To a solution of 3-bromopyridine (39.5 g) in ether (800 mL) at −90° C. (internal temperature) was added n-BuLi (100 mL, 2.5 M) at a rate so that the internal temperature did not exceed −78° C. The resulting mixture was stirred for 1 h at −78° C. and then triisopropoxyborate (59 mL) was added and the resulting mixture was warmed to 0° C. Methanol was added and the mixture was evaporated three times from methanol and then two times from n-propanol. The residue was pumped under high vacuum for 3 days and the resulting foam (76 g of a 1:1 mixture of the title compound:n-propanol) was used as such in the subsequent reaction.

Step 2: 5-Methyl-3-(4-methylsulfonyl)phenyl-2-(3-pyridinyl)pyridine

Following the procedures described in Example 14, but substituting lithium tri-n-propoxy-3-pyridylboronate from Step 1 for 4-chlorophenyl boronic acid, the title compound was obtained as a white solid, m.p. 166–167° C. (2.1 g).

EXAMPLE 17

5-Chloro-2-(4-chlorophenyl)-3-(4-methylsulfonyl)phenylpyridine

Step 1: 2-Amino-3-bromo-5-chloropyridine

To a solution of 2-amino-5-chloropyridine (10 g) in acetic acid (75 mL) at r.t. was added bromine (2.6 mL) slowly. After 30 min, the acid was neutralized by the careful addition of sodium hydroxide (10 N) at 0° C. The resulting orange precipitate was dissolved in ethyl acetate and washed successively with saturated potassium carbonate, saturated $Na_2S_2O_3$ and brine, dried and concentrated. Flash chromatography (eluting with hexane/ethyl acetate, 3:1 v/v) of the residual solid provided the title compound as a pale yellow solid (14.8 g).

Step 2: 2-Amino-5-chloro-3-(4-methylsulfonyl)phenylpyridine

Following the procedures described in Example 1, Steps 2 and 3, but substituting 2-amino-3-bromo-5-chloropyridine from Step 1 (5 g) for 2-amino-3-bromo-5-trifluoromethylpyridine, the title compound was obtained as a white solid (5 g).

Step 3: 2-Bromo-5-chloro-3-(4-methylsulfonyl)phenylpyridine

To a cold (ice bath) solution of 2-amino-5-chloro-3-(4-methylsulfonyl)phenylpyridine (5 g) from Step 2 in water/concentrated HCl (50 mL/10 mL) was added sodium nitrite (1.5 g) in water (10 mL). The resulting mixture was stirred at r.t. for 15 h and the resulting precipitate was removed by filtration and washed successively with water and $CCl_4$. After air drying, the white solid (4.8 g) and $POBr_3$ (10.5 g) in DMF (40 mL) were heated at 100° C. for 2 days. The resulting mixture was poured into ice/water and extracted with ethyl acetate. The aqueous phase was made basic with 1 N NaOH and extracted with ethyl acetate. The combined organics were dried and concentrated. Flash chromatography (eluting with hexane/ethyl acetate, 1:1 v/v) of the residue provided the title compound as a white solid (2.7 g).

Step 4: 5-Chloro-2-(4-chloro)phenyl-3-(4-methylsulfonyl)phenylpyridine

Following the procedures described in Example 3 but substituting 2-bromo-5-chloro-3-(4-methylsulfonyl)phenylpyridine (300 mg) from Step 3 for 2-chloro-3-(4-methylsulfonyl)phenyl-5-trifluoromethylpyridine, the title compound was obtained as a white solid, m.p. 187–188° C. (200 mg).

EXAMPLE 20

5-Chloro-3-(4-methylsulfonyl)phenyl-2-(2-pyridinyl)pyridine

Step 1: 3-Bromo-5-chloro-2-hydroxypyridine

A mixture of 5-chloro-2-hydroxypyridine (100 g) and bromine (40.1 mL) in acetic acid (400 mL) was stirred at r.t. for 1 h. The mixture was poured into 3 L of water and stirred for 30 min then filtered. The residual solid was washed with 2 L of cold water, air dried and then coevaporated with toluene three times and with benzene two times. The white solid (81 g) so obtained was used in the subsequent reaction.

Step 2: 2-Benzyloxy-3-bromo-5-chloropyridine

A mixture of 3-bromo-5-chloro-2-hydroxypyridine (81 g), benzyl bromide (52 mL) and silver carbonate (97 g) in benzene (1 L) was heated at 70° C. for 1 h. The mixture was cooled to r.t. and then filtered through a bed of celite. The filtrate was concentrated and the residual off-white solid was recrystallized from hexane to provide the title compound as a white solid (102 g).

Step 3: 2-Benzyloxy-5-chloro-3-(4-methylsulfonyl)phenylpyridine

Following the procedures described in Example 1, Steps 2 and 3, but substituting 2-benzyloxy-3-bromo-5-chloropyridine (81 g) from Step 2 for 2-amino-3-bromo-5-trifluoromethylpyridine, the title compound was obtained as a white solid (72 g).

Step 4: 5-Chloro-2-hydroxy-3-(4-methylsulfonyl)phenylpyridine

A solution of 2-benzyloxy-5-chloro-3-(4-methylsulfonyl)phenylpyridine (72 g) in trifluoroacetic acid (250 mL) was stirred at 40° C. for 15 min and then poured into ice/water (~1 L). After stirring for 10 min, the white solid was filtered, washed twice with a further 1 L of water and then air dried to provide the title compound.

Step 5: 2,5-Dichloro-3-(4-methylsulfonyl)phenylpyridine

The crude 5-chloro-2-hydroxy-3-(4-methylsulfonyl)phenylpyridine from Step 4 was heated in a sealed bomb at 150° C. with $POCl_3$ (400 mL) for 15 h. After cooling to r.t. the excess $POCl_3$ was removed by distillation under vacuum. The residue was diluted with ethyl acetate and water and then neutralized with sodium hydroxide (10 N) to ~pH 7. The organics were removed, washed with brine and concentrated. The residual solid was recrystallized from ether to provide the title compound as white solid (61 g).

Step 6: Lithium Tri-n-propoxy-2-pyridylbornonate

Following the procedures described in Example 15, Step 1 but substituting 2-bromopyridine (1.9 mL) for 3-bromopyridine, the title compound was prepared as an off-white solid (4.1 g).

Step 7: 5-Chloro-3-(4-methylsulfonyl)phenyl-2-(2-pyridinyl)pyridine

A mixture of 2,5-dichloro-3-(4-methylsulfonyl)phenylpyridine (1 g), lithium tri-n-propoxy-2-pyridylboronate (1.22 g), sodium carbonate (5 mL, 2 M) and bis(triphenylphosphine)palladium dibromide (520 mg) in toluene (100 mL), isopropanol (10 mL) and water (25 mL) was heated at reflux for 7 h. The mixture was cooled to r.t., diluted with ethyl acetate and filtered through a bed of celite. The filtrated was extracted with 6 N HCl and the aqueous was washed with ethyl acetate. The aqueous phase was basified to ~pH 10 with 10 N sodium hydroxide and then extracted with ethyl acetate. The organics were washed with brine, dried and concentrated. Flash chromatography (eluting with hexane/ethyl acetate, 1:1 v/v) of the residue provided the title compound as a white solid, m.p. 134–135° C. (350 mg).

EXAMPLE 21

5-Chloro-3-(4-methylsulfonyl)phenyl-2-(3-pyridinyl)pyridine

Following the procedures described in Example 20, Step 7, but substituting lithium tri-n-propoxy-3-pyridinylboronate from Example 15, Step 1 for lithium tri-n-propoxy-2-pyridinylboronate, the title compound was obtained as a white solid, m.p. 168–169° C.

EXAMPLE 22

5-Chloro-3-(4-methylsulfonyl)phenyl-2-(4-pyridinyl)pyridine

Step 1: Lithium Trimethoxy-4-pyridinylbornonate

Following the procedures described in Example 15, Step 1 but substituting 4-bromopyridine for 3-bromopyridine. The crude material was used prior to evaporating from n-propanol.

Step 2: 5-Chloro-3-(4-methylsulfonyl)phenyl-2-(4-pyridinyl)pyridine

Following the procedures described in Example 20, Step 7, but substituting lithium trimethoxy-4-pyridinylboronate from Step 1 for lithium tri-n-propoxy-2-pyridinylboronate, the title compound was obtained as a white solid, m.p. 187–188° C.

EXAMPLE 23

5-Chloro-3-(4-methylsulfonyl)phenyl-2-(2-methyl-5-pyridinyl)pyridine

Step 1: Trifluoromethanesulfonic acid 2-methylpyridin-5-yl ester

To a mixture of 5-hydroxy-2-methylpyridine (2 g) and pyridine (1.9 mL) in dichloromethane (100 mL) at 0° C. was added trifluoromethanesulfonic acid anhydride (3.4 mL). The mixture was stirred at this temperature for 15 min and then at r.t. for 45 min. Ammonium acetate (25%) was added and the organics were removed and washed with 1 N HCl, dried and concentrated. The title compound was obtained as a beige liquid (4 g) that was used as such.

Step 2: 2-Methyl-5-trimethylstannylpyridine

A mixture of trifluoromethanesulfonic acid 2-methylpyridin-5-yl ester (2.1 g), hexamethylditin (2.85 g), lithium chloride (1.1 g) and palladium tetrakis (triphenylphosphine) (190 mg) was heated at reflux for 180 min and then cooled to r.t. The mixture was filtered through a bed of celite, washing with ethyl acetate. The filtrate was washed twice with 5% potassium fluoride, dried and concentrated. Flash chromatography (eluting with hexane/ethyl acetate, 6:1 v/v) of the residue provided the title compound as a pale yellow oil (1.3 g).

Step 3: 5-Chloro-3-(4-methylsulfonyl)phenyl-2-(2-methyl-5-pyridyl)pyridine

A mixture of 2,5-dichloro-3-(4-methylsulfonyl) phenylpyridine from Example 20, Step 5 (750 mg), 2-methyl-5-trimethylstannylpyridine (1.3 g) and palladium tetrakis(triphenylphosphine) (290 mg) in NMP (10 mL) was heated at 100° C. for 15 h. The mixture was cooled to r.t., diluted with ethyl acetate and filtered through a bed of celite. The filtrate was washed with water, twice with 5% potassium fluoride and then extracted with 1 N HCl. The aqueous phase was neutralized with 10 N sodium hydroxide and then extracted with ethyl acetate. The organics were concentrated and the residue subjected to flash chromatography (eluting with ethyl acetate) to provide the title compound as a white solid, m.p. 127–128° C.

EXAMPLE 43

2-(4-Chlorophenyl)-3-(4-methylsulfonyl)phenylpyridinyl-5-carboxylic acid methyl ester To a solution of 2-(4-chlorophenyl)-5-methyl-3-(4-methylsulfonyl)phenylpyridine (Example 14, 1.9 g) in t-butanol/water (1:2, 60 mL) at 90° C. was added solid potassium permanganate (2.5 g) portionwise over 2 h. The resulting mixture was stirred at 90° C. for 15 h and then cooled to r.t. The mixture was filtered through a bed of celite and the filtrate was acidified to ~pH 2 with 6 N HCl. The white precipitate was filtered and then a portion of this material was taken up in THF/dichloromethane. Diazomethane in ether was added to this solution until there was no more bubbling upon its addition. The resulting mixture was concentrated and subjected to flash chromatography (eluting with hexane/ethyl acetate, 1:1 v/v). The title compound was obtained as a white solid, m.p. 216–218° C.

EXAMPLE 44

2-(4-Chlorophenyl)-3-(4-methylsulfonyl)phenylpyridinyl-5-carboxylic acid

To a solution of 2-(4-chlorophenyl)-3-(4-methylsulfonyl) phenylpyridinyl-5-carboxylic acid methyl ester (140 mg) in ethanol/water (1:1, 10 mL) was added lithium hydroxide (0.35 mL, 3 N) and the resulting mixture was stirred at r.t. for 45 min. Saturated sodium bicarbonate was added and the aqueous was extracted with ethyl acetate. The aqueous phase was treated with 3 N HCl until ~pH 2 and then was extracted with chloroform. The organics were concentrated to provide the title compound as a white solid, m.p. >300° C. (60 mg).

EXAMPLE 45

5-Cyano-2-(4-chlorophenyl)-3-(4-methylsulfonyl) phenylpyridine

To 2-(4-chlorophenyl)-3-(4-methylsulfonyl) phenylpyridinyl-5-carboxylic acid (300 mg) in dichloromethane (10 mL) at reflux was added chlorosulfonylisocyanate (0.4 mL). After 90 min at reflux, the mixture was cooled to r.t. and then DMF (1.5 mL) was added slowly. After 15 min, water was added and the mixture was extracted with ethyl acetate. The organics were washed with water, brine, dried and concentrated. Flash chromatography (eluting with ethyl acetate/hexane, 2:1 v/v) of the residue provided the title compound as a white solid (100 mg). $^1$H NMR (300 MHz, CDCl$_3$) δ 3.06 (s, 3H), 7.21–7.28 (m, 4H), 7.37 (d, 2H), 7.90 (d, 2H), 7.96 (d, 1H), 8.94 (d, 1H).

EXAMPLE 46

5-Chloro-3-(4-methylsulfonyl)phenyl-2-(3-pyridyl)pyridine hydromethanesulfonate

A solution of 5-chloro-3-(4-methylsulfonyl)phenyl-2-(3-pyridyl)pyridine (5.31 g, Example 21) in ethyl acetate (100 mL) was treated with methanesulfonic acid (1 mL) in ethyl acetate (20 mL) dropwise. The resulting precipitate was filtered and dried under vacuum to provide the title compound (6.4 g) as a white solid. $^1$H NMR (300 MHz, CD$_3$OD) δ 2.68 (s, 3H), 3.15 (s, 3H), 7.60 (d, 2H), 7.96–8.00 (m, 3H), 8.14 (d, 1H), 8.47 (dt, 1H), 8.80 (d, 1H), 8.86 (m, 2H).

EXAMPLE 47

5-Chloro-3-(4-methylsulfonyl)phenyl-2-(3-pyridyl)pyridine hydrochloride

A solution of 5-chloro-3-(4-methylsulfonyl)phenyl-2-(3-pyridyl)pyridine (2.05 g, Example 21) in hot ethyl acetate (75 mL) was treated with hydrochloric acid (1.5 mL, 4 M in dioxane) dropwise. The resulting precipitate was filtered and dried under vacuum to provide the title compound (2.2 g) as a white solid. $^1$H NMR (300 MHz, DMSO-d6) δ 3.24 (s, 3H), 7.59 (d, 2H), 7.80 (dd, 1H), 7.91 (d, 2H), 8.15 (d, 1H), 8.22 (d, 1H), 8.69 (d, 1H), 8.77 (d, 1H), 8.90 (d, 1H).

EXAMPLE 59

5-Chloro-3-(4-methylsulfonyl)phenyl-2-(2-methyl-5-pyridinyl)pyridine Hydrochloride Following the procedure described in Example 47, but substituting 5-chloro-3-(4-methylsulfonyl)phenyl-2-(2-methyl-5-pyridinyl)pyridine (from Example 23) for 5-chloro-3-(4-methylsulfonyl)phenyl-2-(3-pyridyl)pyridine, the title compound was obtained as a white solid. $^1$H NMR (300 MHz, DMSO-d$_6$): δ 2.68 (s, 3H), 3.25 (s, 3H), 7.61 (d, 2H), 7.70 (d, 1H), 7.92 (d, 2H), 8.07 (dd, 1H), 8.21 (d, 1H), 8.54 (d, 1H), 8.88 (d, 1H).

EXAMPLE 71

5-Chloro-3-(4-methylsulfonyl)phenyl-2-(2-ethyl-5-pyridinyl)pyridine

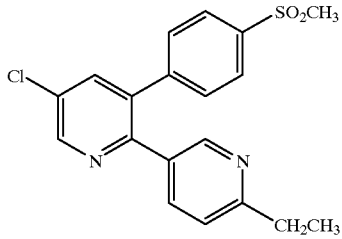

Step 1: Lithium Tri-n-propoxy-2-ethyl-5-pyridylboronate

Following the procedures described in Example 15 Step 1 but substituting 2-ethyl-5-bromopyridine (Tilley and Zawoiski, *J. Org. Chem.* 1988, 53, 386) (4.6 g) for 3-bromopyridine, the title compound was prepared as a yellow solid.

Step 2: 5-Chloro-3-(4-methylsulfonyl)phenyl-2-(2-ethyl-5-pyridinyl)pyridine

A mixture of 2,5-dichloro-3-(4-methylsulfonyl)phenylpyridine (Example 20 Step 5) (5.6 g), lithium tri-n-propoxy-2-ethyl-5-pyridylboronate (Step 1) (4.0 g), sodium carbonate (17 mL, 2 M) and bis(triphenylphosphine)palladium dibromide (420 mg) in toluene (75 mL), ethanol (75 mL) and water (15 mL) was heated at reflux for 7 h. The mixture was cooled to r.t., diluted with ethyl acetate and filtered through a bed of celite. The filtrate was extracted with 6 N HCl and the aqueous was washed with ethyl acetate. The aqueous phase was basified to ~pH 10 with 10 N sodium hydroxide and then extracted with ethyl acetate. The organics were washed with brine, dried and concentrated. Flash chromatography (eluting with hexane/ethyl acetate, 1:1 v/v) of the residue provided the title compound as a white solid (4.0 g). $^1$H NMR (500 MHz, acetone-d$_6$) δ 1.21 (t, 3H), 2.74 (q, 2H), 3.14 (s, 3H), 7.14, (d, 1H), 7.59 (m, 3H), 7.93 (d, 2H), 7.99 (d, 1H), 8.44 (d, 1H), 8.75 (d, 1H).

EXAMPLE 71

Alternate Method
5-Chloro-3-(4-methylsulfonyl)phenyl-2-(2-ethyl-5-pyridinyl)pyridine

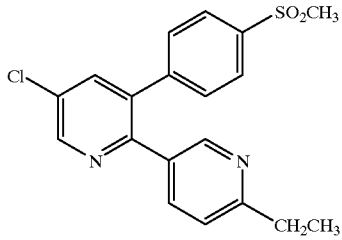

Step 1: 5-Bromo-2-ethylpyridine 280 mL of 5 N sodium hydroxide (1.4 mol, 2.09 eq) was added to a solution of 158 g of 2,5-dibromopyridine (0.67 mol, 1 eq) in 1.4 L of THF. To the resulting solution, 700 mL of 1 N triethylboron in THF (0.70 mol, 1.04 eq), 195 mg of bis(acetonitrile)palladium(II) chloride (0.75 mmol, 0.0011 eq) and 414 mg 1,1'-bis(diphenylphosphino)ferrocene (0.75 mmol, 0.0011 eq) were added. The reaction was slowly heated to a very slight reflux for 3 hours. It was then cooled down to 0° and treated sequentially with 140 mL of 5 N sodium hydroxide (0.70 mol, 1.04 eq) and 53 mL of 30% hydrogen peroxide (0.70 mol, 1.05 eq) at such a rate that the temperature never exceeded 10° C. The mixture was extracted with ether, and the ether extracts washed with sodium hydroxide, water, brine and dried over MgSO$_4$. The ether solution was then concentrated and the brown residue was distilled under vacuum (40° C., 1 Torr) to give 112 g of the title compound as a clear oil slightly contaminated with the starting material and 2,5-diethylpyridine. Yield ~90%. The $^1$H NMR is comparable to that reported by J. W. Tilley and S. Zawoiski; *J. Org. Chem.*, 1988, 53, 386–390. The material is suitable for use in the next step without further purification.

Step 2: Lithium Tri-n-propoxy-2-ethyl-5-pyridylboronate

Following the procedures described in Example 15 Step 1 but substituting 5-bromo-2-ethylpyridine from Step 1 for 3-bromopyridine, the title compound was prepared as a yellow solid.

Step 3: 5-Chloro-3-(4-methylsulfonyl)phenyl-2-(2-ethyl-5-pyridinyl)pyridine

A mixture of 2,5-dichloro-3-(4-methylsulfonyl)phenylpyridine (Example 20 Step 5) (5.6 g), lithium tri-n-propoxy-2-ethyl-5-pyridylboronate (Step 2) (4.0 g), sodium carbonate (17 mL, 2 M) and bis(triphenylphosphine)palladium dibromide (420 mg) in toluene (75 mL), ethanol (75 mL) and water (15 mL) was heated at reflux for 7 h. The mixture was cooled to r.t., diluted with ethyl acetate and filtered through a bed of celite. The filtrate was extracted with 6 N HCl and the aqueous was washed with ethyl acetate. The aqueous phase was basified to ~pH 10 with 10 N sodium hydroxide and then extracted with ethyl acetate. The organics were washed with brine, dried and concentrated. Flash chromatography (eluting with hexane/ethyl acetate, 1:1 v/v) of the residue provided the title compound as a white solid (4.0 g). $^1$H NMR (500 MHz, acetone-d$_6$) δ 1.21 (t, 3H), 2.74 (q, 2H), 3.14 (s, 3H), 7.14, (d, 1H), 7.59 (m, 3H), 7.93 (d, 2H), 7.99 (d, 1H), 8.44 (d, 1H), 8.75 (d, 1H).

EXAMPLE 72

5-Chloro-3-(4-methylsulfonyl)phenyl-2-(2-ethyl-5-pyridinyl)pyridine hydromethanesulfonate

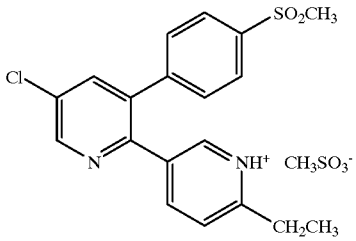

A solution of 5-chloro-3-(4-methylsulfonyl)phenyl-2-(2-ethyl-5-pyridinyl)pyridine (3.4 g, Example 71) in ethyl acetate (40 mL) and ether (100 mL) was treated with methanesulfonic acid (873 mg) in ether (20 mL) dropwise. The resulting precipitate was cooled to −20° C., filtered and dried under vacuum to provide the title compound (4.3 g) as a white solid. $^1$H NMR (500 MHz, CD$_3$OD) δ 1.40 (t, 3H), 2.68 (s, 3H), 3.07 (q, 2H), 3.15 (s, 3H), 7.60 (d, 2H), 7.86 (d, 1H), 7.99 (d, 2H), 8.11 (d, 1H), 8.34 (m, 1H), 8.69 (d, 1H), 8.83 (d, 1H).

EXAMPLE 73
5-Chloro-3-(4-methylsulfonyl)phenyl-2-(2-cyclopropyl-5-pyridinyl)pyridine $^1$H NMR (acetone-d$_6$) δ 0.9 (m, 4H), 2.0 (m, 1H), 3.14 (s, 3H), 7.15 (d, 1H), 7.50 (dd, 1H), 7.59 (m, 2H), 7.95 (m, 3H), 8.36 (d, 1H), 8.72 (d, 1H).

EXAMPLE 74
5-Chloro-3-(4-methylsulfonyl)phenyl-2-(2,6-dimethyl-3-pyridinyl)pyridine

| Analysis for: | C | H | N |
|---|---|---|---|
| Calculated | 61.20 | 4.60 | 7.51 |
| Found | 61.52 | 4.52 | 7.87 |

ALTERNATIVE METHODS OF PREPARATION

Below are exemplified additional methods of preparation. The examples are intended to be read independently. In particular, each example uses a compound numbering scheme that is internally consistant, but is not necessarily consistant with the other examples or other portions of the specification.

PREPARATION OF EXAMPLE 21
5-Chloro-3-(4-methylsulfonyl)phenyl-2-(3-pyridinyl)pyridine Example 21

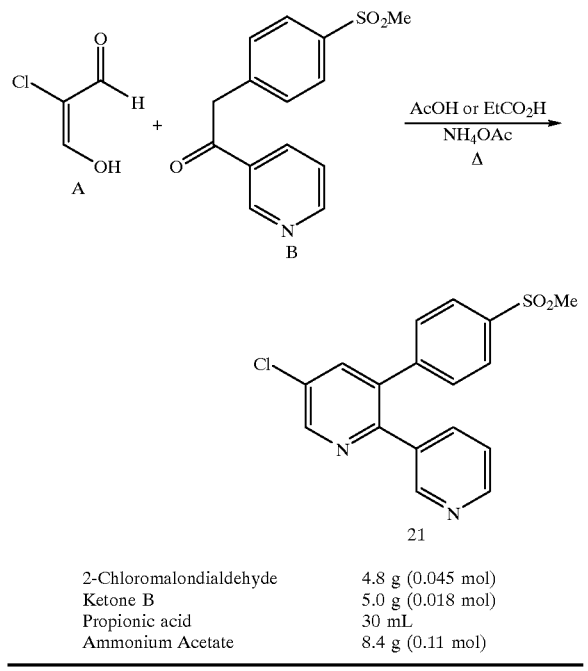

| 2-Chloromalondialdehyde | 4.8 g (0.045 mol) |
| Ketone B | 5.0 g (0.018 mol) |
| Propionic acid | 30 mL |
| Ammonium Acetate | 8.4 g (0.11 mol) |

A mixture of ketone B (5.0 g), 2-chloromalondialdehyde (4.8 g) and ammonium acetate in propionic acid were heated to 130° C. The acetic acid produced was removed by distillation and heating continued at 136° C. for 15 hours. The reaction mixture was basified with sodium carbonate, water was added and the product was extracted into dichloromethane (2×150 mL). The organic layers were carbon treated (Dowex), dried (MgSO$_4$) and the solvent removed to afford 21 as an off white solid (3.4 g, 55% yield).

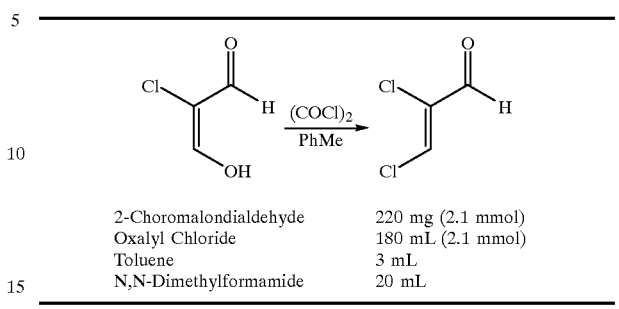

| 2-Choromalondialdehyde | 220 mg (2.1 mmol) |
| Oxalyl Chloride | 180 mL (2.1 mmol) |
| Toluene | 3 mL |
| N,N-Dimethylformamide | 20 mL |

N,N-dimethyl formamide was added to a slurry of 2-chloromalondialdehyde (220 mg) in toluene. Oxalyl chloride was added and the reaction mixture was stirred until complete dissolution occurred.

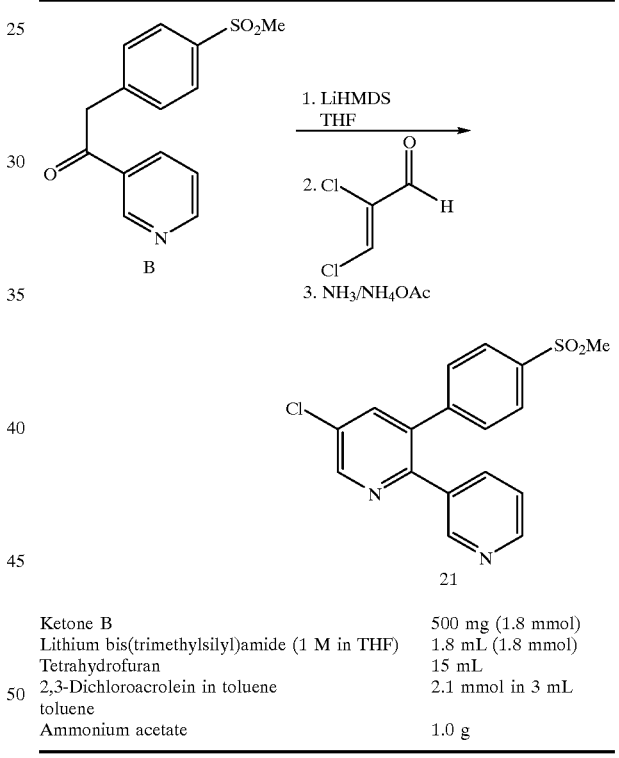

| Ketone B | 500 mg (1.8 mmol) |
| Lithium bis(trimethylsilyl)amide (1 M in THF) | 1.8 mL (1.8 mmol) |
| Tetrahydrofuran | 15 mL |
| 2,3-Dichloroacrolein in toluene | 2.1 mmol in 3 mL toluene |
| Ammonium acetate | 1.0 g |

Lithium bis(trimethylsilyl)amide (1.8 mL; 1 M in THF) was added dropwise to ketone B (500 mg) in THF (15 mL) at −78° C. The reaction mixture was warmed to ambient temperature for 1 hour to form the lithium enolate of B before recooling to −78° C. A solution of 2,3-dichloroacrolein was added and the temperature allowed to warm to room temperature. After 1 hour ammonia gas was passed through the solution and after 30 minutes ammonium acetate (1 g) was added. The reaction mixture was warmed to 60° C. for 1 hour and poured into aqueous sodium hydroxide (2 M; 100 mL). The product was extracted with dichloromethane (2×150 mL), dried (MgSO4) and the solvent removed to afford 21 (500 mg; 80%).

PREPARATION OF STARTING MATERIALS

PREP 1

Synthesis of (4-methylsulfonyl)phenylacetic acid

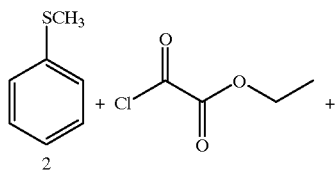

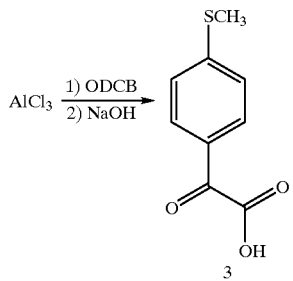

| | |
|---|---|
| Thioanisole 2 (FW = 124.2, d = 1.058) | 50.00 g (0.403 mol, 47.3 mL) |
| Ethyloxalyl chloride (FW = 136.5, d = 1.222) | 82.43 g (0.604 mol, 67.5 mL) |
| Aluminum chloride (FW = 133.3) | 75.13 g (0.564 mol) |
| o-dichlorobenzene (ODCB) | 112 mL |

The ethyloxalyl chloride and ODCB were charged to a flask equipped with an overhead mechanical stirrer and cooled to 0° C. The AlCl₃ was added slowly. The addition of the AlCl₃ was exothermic. The thioanisole 2 was added dropwise via an addition funnel over 1.5 h. The reaction mixture rapidly turns a dark violet color. This addition was also exothermic.

After 1 h, the reaction was complete by HPLC. The reaction was quenched by the slow addition of 300 mL of 1 N HCl at 0° C. After warming to room temperature, water and ODCB (50 mL each) were added. The layers were mixed and cut. The organic (bottom) phase was washed with 1×250 mL water and then dried over MgSO₄.

This quench was also exothermic. The reaction mixture turned from dark violet to pale green during the quench. The dried ODCB solution was charged to a Morton flask equipped with mechanical stirring. A solution of 1 N NaOH (800 mL) was added. The biphasic mixture was stirred vigorously and heated to 50° C. Hydrolysis to 3 was complete in 2–3 h by HPLC. The product-containing aqueous phase was taken directly into the Wolf-Kishner reaction.

(4-Methylthio)phenylacetic acid

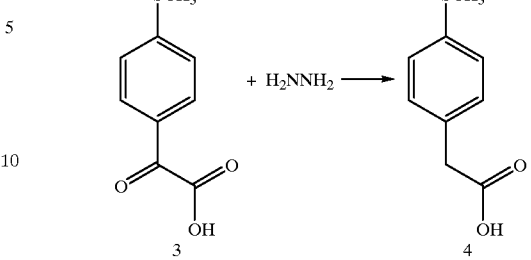

| | |
|---|---|
| 3 (in 1N NaOH solution) | (0.402 mol) |
| Hydrazine (FW = 32.1, 35 wt % in water) | 206.14 g (2252 mol, 204 mL) |
| NaOH (5N solution) | 5 mL |

The hydrazine and NaOH were charged to a Morton flask equipped with mechanical stirring. After heating the hydrazine solution to 75° C., the solution of 3 in NaOH was added over 35–40 min. At the end of the addition the reaction mixture was brought to reflux for 5 days. HPLC showed the reaction to be ca. 95% complete at this point. The starting material was largely consumed in under 24 h, but a third peak appeared which took several days to convert to 4. The reaction was acidified with concentrated HCl to pH=1.5 and extracted with EtOAc (1×750 mL and 1×250 mL). The combined product-containing organic phases were washed 2×250 mL 1 N HCl.

On acidification, the reaction mixture turned bright yellow.

(4-Methylsulfonyl)phenylacetic acid

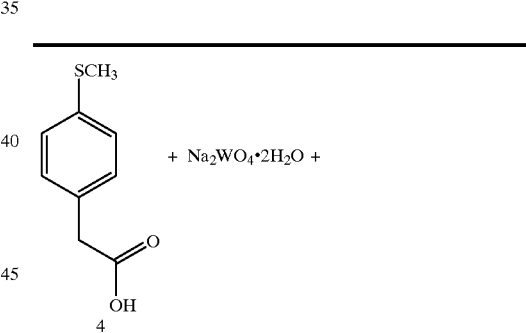

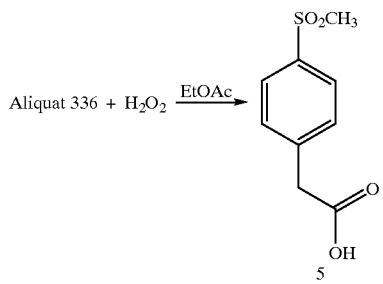

| | |
|---|---|
| (4-Methylthio)phenylacetic acid 4 (FW = 182.3) | (0.402 mol) |
| Na₂WO₄·H₂O (FW = 329.9) | 2.64 g (0.008 mol) |
| Aliquat 336 (FW = 404) | 8.08 g (0.020 mol) |
| Hydrogen peroxide (FW = 34.0, 30 wt % in water) | 136 g (1.200 mol, 123 mL) |

A flask equipped for mechanical stirring was charged with 4 (from reaction above, in EtOAc), Aliquat 336, and Na$_2$WO$_4$·2H$_2$O (dissolved in ca. 15 mL H$_2$O). Hydrogen peroxide was added slowly via an addition funnel over ca. 30 min. Completion of reaction was checked by HPLC. The reaction was washed with 2×400 mL H$_2$O and dried over MgSO$_4$. Quantification of product in the organic layer gave 61.29 g 5 (71% yield from thioanisole). On concentration of the solution, a white solid precipitated. The slurry was filtered, and washed with hexanes. Recovery was 49.02 g 5 (57% from thioanisole).

Ivanov-Claisen Condensation for the Preparation of 1-(3-pyridyl)-2-((4-methylsulfonyl)phenyl)ethane-1-one

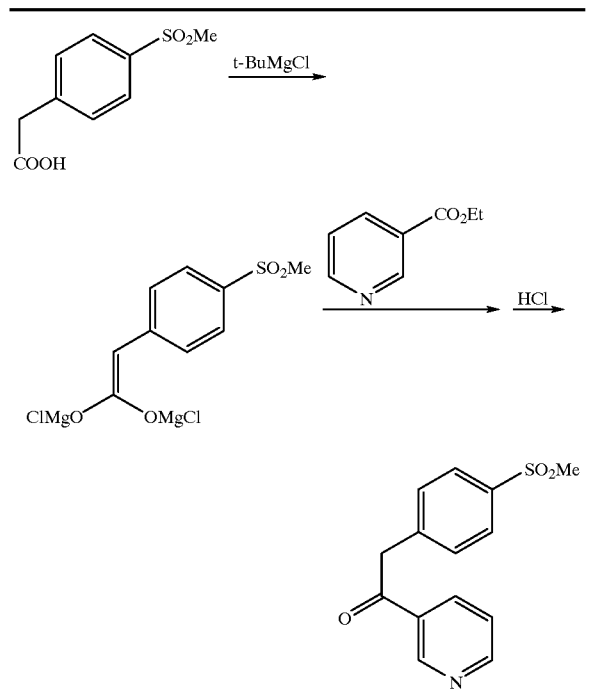

(4-Methylsulfonyl)benzyl-3-pyridylketone from ethyl nicotinate and (4-methylsulfonyl)phenylacetic acid

| | |
|---|---|
| (4-Methylsulfonyl)phenyl Acetic Acid (MW = 217) | 10 g (46.7 mmol) |
| t-Butyl magnesium chloride (1N/THF) | 128.11 ml (128.11 mmol) |
| Ethyl nicotinate (MW = 151.2; d = 1.107) | 5.54 ml (39.4 mmol) |
| THF | 400 ml |

(4-Methylsulfonyl)phenylacetic acid was dissolved in THF under nitrogen and 1.9 equivalents (88.73 ml) of t-butyl magnesium chloride were added over 5 minutes to the solution. The reaction was exothermic and the temperature rose from 20° C. to 50° C. After addition of the first equivalent of t-butyl magnesium chloride, the solution turned red.

The reaction temperature was maintained at 50° C. After one hour, 0.5 equivalents of ethyl nicotinate were added. The solution turned yellow and a white precipitate formed. After one hour, 0.5 equivalents of t-butyl magnesium chloride were added at 50° C. The solution turned red. This sequence of addition was repeated using 0.25 eq., 0.125 eq., 0.0625 eq. of ethyl nicotinate and t-butyl magnesium chloride. The reaction mixture was aged for 1 hour between each addition.

After the last addition, the reaction was quenched by adding the reaction mixture into vigorously stirred 2 N hydrochloric acid (100 ml). The solids at the bottom of the reaction mixture dissolved with effervescence when stirred in hydrochloric acid.

The pH of the aqueous phase of the reaction mixture was adjusted to 10 with sodium carbonate. LC assay showed 91% yield of ketone Preparation of (4-Methylsulfonyl)benzaldehyde The preparation follows the procedure of Ulman JOC, pp4691 (1989).

(4-Methylsulfonyl)benzaldehyde from 4-fluorobenzaldehyde

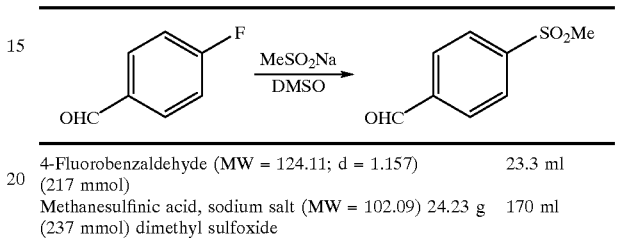

| | |
|---|---|
| 4-Fluorobenzaldehyde (MW = 124.11; d = 1.157) (217 mmol) | 23.3 ml |
| Methanesulfinic acid, sodium salt (MW = 102.09) 24.23 g (237 mmol) dimethyl sulfoxide | 170 ml |

Reagents were added to dimethyl sulfoxide and heated to 130° C. for 18 hrs. The sodium methanesulfonate was partially insoluble at RT but went into solution at 130° C. Sodium fluoride precipitated out of solution. The reaction mixture was poured into 300 ml water. The product precipitated out as a white solid. The reaction mixture was filtered. The product recovered was washed with 100 ml water and 2×50 ml methanol to remove dimethyl sulfoxide. The solvent was evaporated from the product under reduced pressure affording 39.9 g of the title compound as a white powder (86% isolated yield). C$^{13}$-NMR (CDCl$_3$): 44.33, 128.25, 130.43, 139.70, 145.38, 190.72.

4-Methylsulfonylbenzaldehyde from 4-Chlorobenzaldehyde

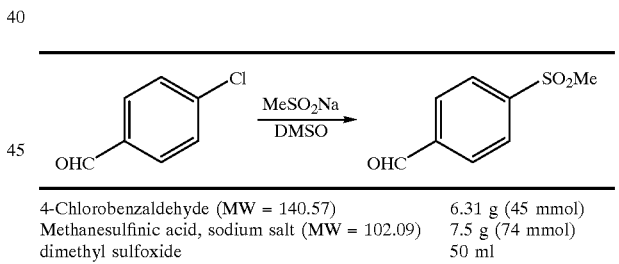

| | |
|---|---|
| 4-Chlorobenzaldehyde (MW = 140.57) | 6.31 g (45 mmol) |
| Methanesulfinic acid, sodium salt (MW = 102.09) | 7.5 g (74 mmol) |
| dimethyl sulfoxide | 50 ml |

Reagents were added to dimethyl sulfoxide and heated to 130° C. for 18 hrs.

The sodium methanesulfinate was partially insoluble at RT but went into solution at 130° C. Sodium chloride precipitated out of solution. The reaction mixture was poured into 100 ml water. The product precipitated out as a white solid. The reaction mixture was filtered. The product recovered was washed with 50 ml water and 2×25 ml methanol to remove dimethyl sulfoxide. The solvent was evaporated from the product under reduced pressure affording 5.1 g of (4-methylsulfonyl)benzaldehyde as a white powder (62% isolated yield).

Homer/Wittig Route for the Preparation of 1-(3-pyridyl)-2-((4-methylsulfonyl)phenyl)ethane-1-one

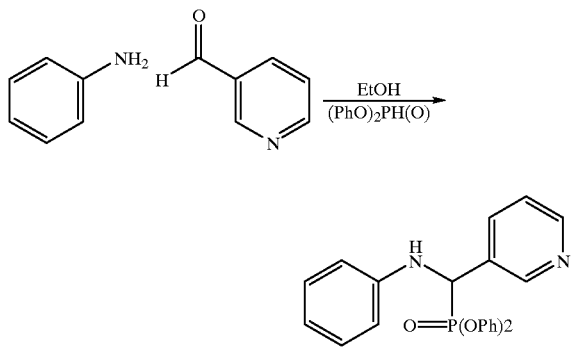

Ref: H. Zimmer, J. P. Bercz, Liebigs Ann. Chem. 1965, 686, 107–114.

| Aniline | 89.4 g (0.96 mol) |
| 3-pyridinecarboxaldehyde | 102.8 g (0.96 mol) |
| Ethanol | 150 mL |
| Diphenylphosphite | 224.7 g (0.96 mol) |

A solution of aniline in ethanol (50 mL) was added to a solution of 3-pyridine carboxaldehyde in ethanol (100 mL) at 0° C. After 2 hours diphenylphosphite was added and stirring was continued at room temperature for 18 hours. Methyl tert-butylether (400 mL) was added to further precipitate the product which was filtered, washed (MTBE) and dried under vacuum to afford 320 g (80%) of the pyridylamino diphenylphosphonate as a white solid. $^{13}$C NMR (CDCl3):

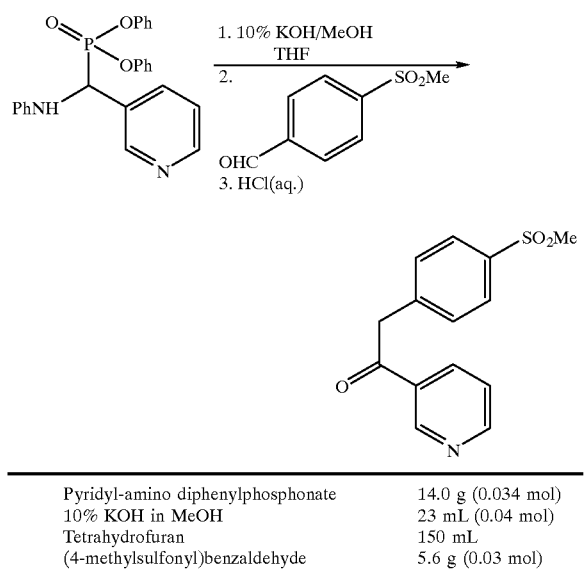

| Pyridyl-amino diphenylphosphonate | 14.0 g (0.034 mol) |
| 10% KOH in MeOH | 23 mL (0.04 mol) |
| Tetrahydrofuran | 150 mL |
| (4-methylsulfonyl)benzaldehyde | 5.6 g (0.03 mol) |

10% KOH/MeOH (23 mL) was added over 10 minutes to a solution of the phosphonate (14.0 g) in tetrahydrofuran at −45° C. After a further 10 minutes the benzaldehyde was added in one portion and after 1 hour the reaction mixture was allowed to warm to ambient temperature. Aqueous hydrochloric acid (2 N, 100 mL) was added and the solution was left standing for 18 hours. EtOAc (200 mL) and water (200 mL) were added and the organic layer discarded. The acid layer wash was basified (pH=9) with sodium carbonate and extracted with dichloromethane (2×150 mL). The organic layers were combined, dried (MgSO4) and concentrated. Trituration with hexanes afforded (4-methylsulfonyl) benzyl-3-pyridyl ketone as a pale yellow solid (6.3 g; 76%). $^{13}$C NMR (D-6 DMSO): 196.4, 153.6, 149.4, 140.8, 139.1, 135.7, 131.5, 130.9, 126.8, 123.9, 44.6 and 43.5 ppm.

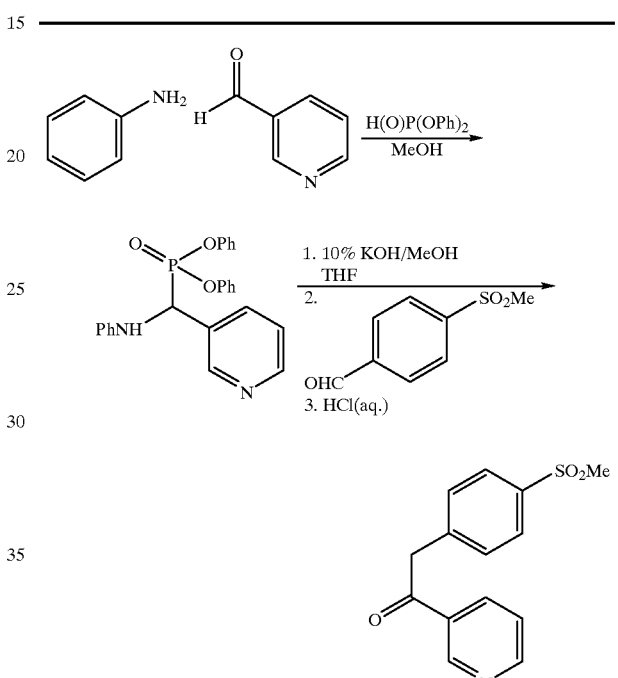

| Aniline | 4.47 g (0.05 mol) |
| 3-pyridinecarboxaldehyde | 5.36 g (0.05 mol) |
| Methanol | 10 mL |
| Diphenylphosphite | 11.2 g (0.05 mol) |
| 10% KOH in MeOH | 28 mL (0.05 mol) |
| (4-methylsulfonyl)benzaldehyde | 8.3 g (0.45 mol) |

A solution of aniline in methanol (5 mL) was added to a solution of 3-pyridine carboxaldehyde in methanol (5 mL) at 0° C. After 2 hours diphenylphosphite was added and stirring was continued at room temperature for 18 hours. THF (100 mL) was added and the reaction ws cooled to −40° C. 10% KOH/methanol (28 mL) was added and after 30 minutes (4-methylsulfonyl)benzaldehyde (8.3 g) was added. The reaction was allowed to warm to room temperature and stirred for 18 hours. EtOAc (200 mL) and water (200 mL) were added and the organic layer discarded. The acid layer was basified (pH=9) with sodium carbonate and extracted with dichloromethane (2×150 mL). The organic layers were combined, dried (MgSO$_4$) and concentrated. Trituration with hexanes afforded (4-methylsulfonyl) benzyl-3-pyridyl ketone as a pale yellow solid (9.7 g; 71%).

PREPARATION OF CHLOROMALONDIALDEHYDE

A number of routes are available for the preparation of chloromalondialdehyde.

Preparation from 1,1,2,3,3-Pentachloropropane

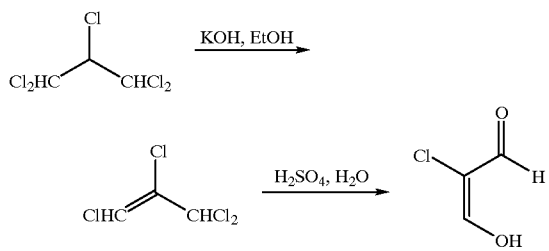

A detailed experimental is published in Houben-Weyl-Muller: Methoden der Organischen Chemie, 4th Edit., Vol 7/1, Thieme Verlag, Stuttgart, 1954, page 119. The starting material 1,1,2,3,3-pentachloropropane is commercially available from Pfaltz and Bauer.

Preparation from Mucochloric Acid

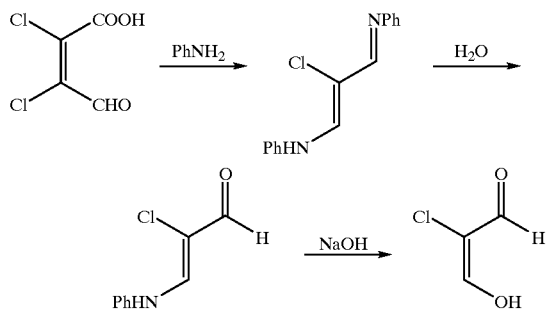

The following is a slight variation of the original procedure of Dieckmann (Ber. Deut. Chem. Ges. 1904, 37, 4638).

| | | |
|---|---|---|
| Mucochloric acid | 50.0 g (0.30 mol) | |
| Aniline | 54 mL (0.60 mol) | |
| Water | 1000 mL | |

To a solution of aniline in water at 85° C. in a vigorously stirred 2 L flask was added mucochloric acid in small portions over 30 min. On addition of the mucochloric acid, a yellow color develops, which quickly dissipated. The reaction mixture stayed heterogeneous and filtration of an aliquot after 30 min heating indicated completion of the reaction.

The reaction mixture was heated at 90° C. for 60 min., cooled to 50° C. and filtered. The filtercake was washed with 50 mL of 2 N HCl and 100 mL of $H_2O$. The product was dried in a $N_2$ stream to give 57 g (100% yield) of 3-anilido-2-chloro-acrolein as a gray solid. $^{13}C$ NMR ($D_6$-DMSO in ppm): 108, 117, 124, 129, 140. 147, 182.

| | | |
|---|---|---|
| 3-Anilido-2-chloro-acrolein | 57 g (0.30 mol) | |
| 5N NaOH solution | 120 mL (0.6 mol) | |

A solution of 3-anilido-2-chloro-acrolein in 120 mL of 5 N NaOH was heated to 100° C. for 90 min. The dark black solution was extracted twice with 50 mL each of MTBE.

The first organic wash removed most of the dark color from the solution, and the second organic wash was only lightly colored.

On cooling the aqueous phase, a crystalline precipitate formed. This product was the 3-chloromalondialdehyde Na salt.

The aqueous phase was acidified by the addition of 60 mL of 37% HCl solution. The aqueous phase was extracted (MTBE/THF 50/50, 400 mL total) and the combined organic phases were dried over MgSO4. After treatment with Darco G60 and filtration through a plug of SiO2, the solution was evaporated to give 19.6 g (62% overall yield) of chloromalondialdehyde as a dark solid. Recrystallization from ca. 10 mL of MTBE gave 11.13 g of pure chloromalondialdehyde as a tan solid. $^{13}C$ NMR ($D_6$-DMSO in ppm): 113, 175 (broad).

Preparation from Chloroacetylchloride

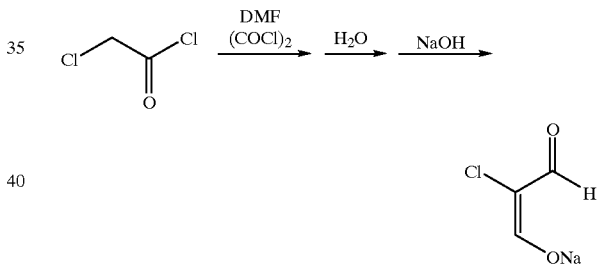

Arnold (Collect. Czech. Chem. Commun. 1961, 26, 3051) mentions the formation of 3-dimethylamino-2-chloro-acrolein by reaction of chloroacetic acid with the Vilsmeyer reagent derived from $POCl_3$ and DMF. A variation and extension of his procedure prepares chloromalondialdehyde as its Na salt.

Oxalyl chloride (280 mL, 3.2 mol) was added at 10° C. to 1000 mL of DMF. The reaction was highly exothermic and a heavy precipitate formed. After a 2 h age, chloroacetylchloride (110 mL, 1.4 mol) was added and the reaction mixture was warmed to 75° C. for 3 hours. Analysis of an aliquot by $^1H$ NMR indicated complete consumption of the chloroacetylchloride and the reaction mixture was quenched by addition into 1 L of $H_2O$. To the cooled solution was added 500 mL of a 50% NaOH solution. The reaction mixture was heated to reflux for 5 hours. On cooling a precipitate formed, which was filtered and washed with water. The tan solid was dried in a $N_2$ stream to give 84 g of the sodium salt of chloromalondialdehyde as a tan solid (54% yield).

PREPARATION OF EXAMPLE 23

Step 1: Preparation of Weinreb amide

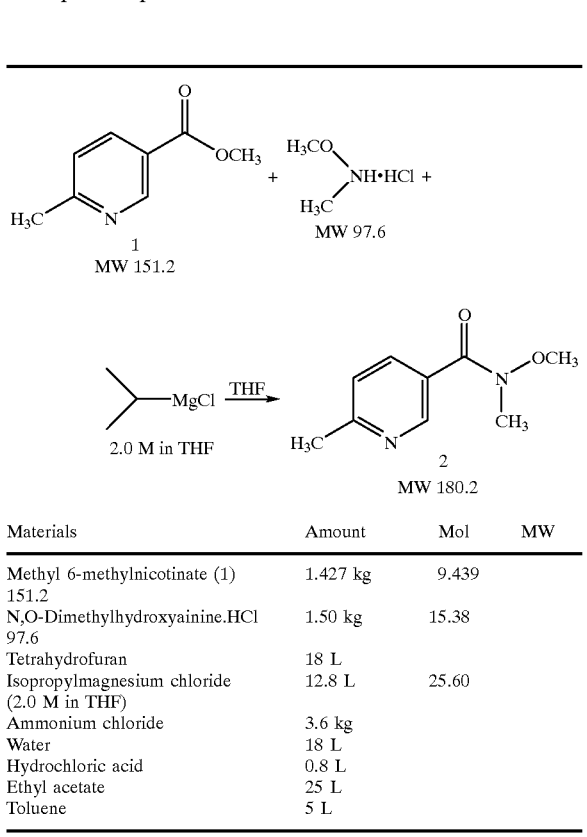

| Materials | Amount | Mol | MW |
|---|---|---|---|
| Methyl 6-methylnicotinate (1) 151.2 | 1.427 kg | 9.439 | |
| N,O-Dimethylhydroxyainine.HCl 97.6 | 1.50 kg | 15.38 | |
| Tetrahydrofuran | 18 L | | |
| Isopropylmagnesium chloride (2.0 M in THF) | 12.8 L | 25.60 | |
| Ammonium chloride | 3.6 kg | | |
| Water | 18 L | | |
| Hydrochloric acid | 0.8 L | | |
| Ethyl acetate | 25 L | | |
| Toluene | 5 L | | |

Methyl 6-methylnicotinate (1) (1.42 kg, 9.44 mol), N,O-dimethylhydroxylamine.HCl (1.50 kg, 15.38 mol), and tetrahydrofuran (18 L) are added to a 100 L flask. The mixture is cooled to −20° C.

Isopropylmagnesium chloride (12.8 L, 25.6 mol) is added over 1 h maintaining the temperature below −18° C.

The reaction is essentially complete within 25 min after the addition. The reaction mixture is added to aqueous ammonium chloride (20 wt %, 18 L) at 5° C. in a 180 L Pflaubler.

The pH is adjusted to ~7.0 (6.95) by the addition of concentrated hydrochloric acid (0.8 L) and the mixture is stirred for 20 min. The layers are separated.

The aqueous layer is extracted with ethyl acetate (2×10 L and 1×5 L). The organic layers (~60 L) are concentrated under vacuum (23" Hg) at 50° C. Toluene (3 L) is added to the residue and the solution is concentrated again. Solid impurities are removed by filtration through a frit and are washed with toluene (2 L). The filtrate is concentrated to afford the Weinreb amide 2 as a dark red oil (assay 1.78 kg, 92 wt %, >99% yield).

Step 2: DIBAL Reduction of Weinreb Amide 2 to 6-Methylnicotinaldehyde (3)

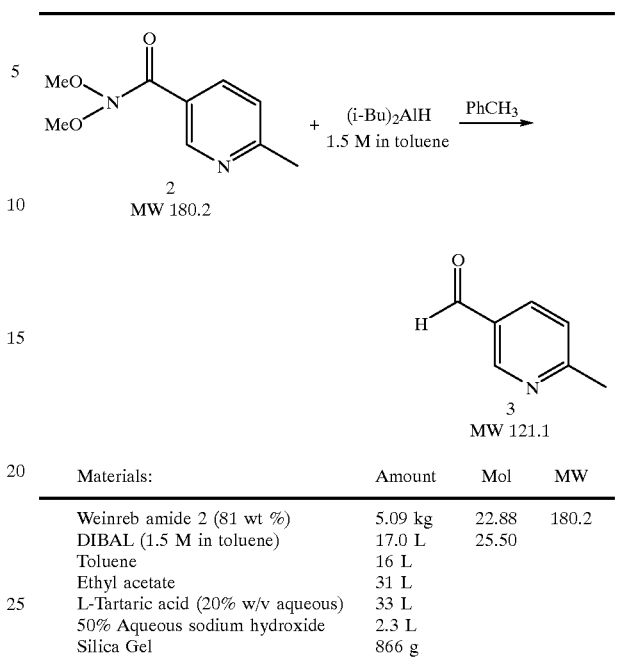

| Materials: | Amount | Mol | MW |
|---|---|---|---|
| Weinreb amide 2 (81 wt %) | 5.09 kg | 22.88 | 180.2 |
| DIBAL (1.5 M in toluene) | 17.0 L | 25.50 | |
| Toluene | 16 L | | |
| Ethyl acetate | 31 L | | |
| L-Tartaric acid (20% w/v aqueous) | 33 L | | |
| 50% Aqueous sodium hydroxide | 2.3 L | | |
| Silica Gel | 866 g | | |

The Weinreb amide 2 (4.12 assay kg, 22.88 mol) is dissolved in toluene (16 L) in a 72 L glass, round-bottomed flask equipped with overhead stirring, a 5 L addition funnel, thermocouple probe, and a nitrogen inlet. The solution is cooled to −20° C. under nitrogen and diisobutylaluminum hydride (17 L, 1.5 M in toluene, 25.5 mol) is added over 2.5 h. The reaction temperature is maintained at <−5° C. during the course of the addition. When the addition is complete the reaction is sampled.

Excess diisobutylaluminum hydride is quenched by the addition of ethyl acetate (3.0 L). The reaction is aged for 30 min at −10° C. to 0° C. and then added to a 20% tartaric acid solution (33 L) at 20° C.–25° C. over 15 min using cooling to maintain the temperature <30° C.

The reaction vessel is rinsed with toluene (1.0 L) and the rinse is added to the quench solution. The mixture is aged for 1 hour at 20–25° C. with efficient stirring. Two clear liquid phases are present. The pH is adjusted to 8.0 with 50% sodium hydroxide (2.3 L) and the mixture is aged with stirring for another 30 min. The layers are separated and the aqueous layer is extracted with ethyl acetate (26 L).

The toluene layer (~38 L) is concentrated under vacuum (29.5" Hg) at 10–14° C. until the batch temperature reaches 30° C. The ethyl acetate extract is then added and the concentration is continued at 0–10° C. (29.5" Hg) to a final volume of ~7 L. The remaining solution is filtered through silica gel (866 g, 230–400 mesh). The concentrating flask is rinsed with ethyl acetate (4 L) and the rinse is used to wash the cake. The cake is then washed with more ethyl acetate (6 L).

The combined filtrate and washes are transferred into a clean 22 L flask through a 5 micron filter and concentrated under vacuum (29.5") at 0–5° C. The concentration is continued until the batch temperature reaches 34° C. The liquid (4.08 kg, 60.8 wt %, 90% assay yield) is used as is in the next step.

Step 3: Synthesis of the N,P-acetal 4

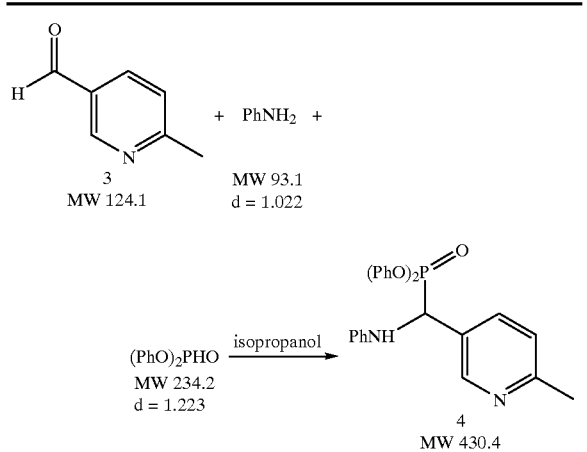

| Materials | Amount | Mol | MW |
|---|---|---|---|
| 6-Methylnicotinaldehyde (3) (55 wt %) | 4.032 kg | 18.02 | 124.1 |
| Aniline (99%) | 2.96 L | 32.15 | 93.1 |
| Diphenylphosphite (10–15% phenol) | 7.6 L | ~35.0 | 234.2 |
| 2-Propanol | 15 L | | |
| n-Heptane | 60 L | | |

A 100 L flask is equipped with a mechanical stirrer, thermocouple, 5 L dropping-funnel, and nitrogen inlet. 6-Methylnicotinaldehyde (2.238 assay kg, 18.02 mol) is dissolved in 2-propanol (5 L). Aniline (2.96 L, 32.15 mol, 1.8 equiv) is added in one portion (internal temperature: 16° C.) followed by the dropwise addition of diphenylphosphite (7.6 L, ~35.0 mol, ~2 equiv) over 45 min. The diphenylphosphite contains 10–15% phenol.

Additional 2-propanol (5 L) is added followed by the slow addition of n-heptane (40 L). The N,P-acetal 4 precipitates from solution The mixture is cooled in an ice-bath at 5° C. The N,P-acetal is filtered and washed with n-heptane/2-propanol (4:1; 25 L). The resulting pale-white solid is dried for 24 h under low vacuum with a flow of nitrogen affording 6.214 kg (90.7 wt %, 5.636 assay kg, 13.1 mol, 72.5% yield) of product.

Step 4: Synthesis of (4-Methylsulfonyl)benzaldehyde (6)

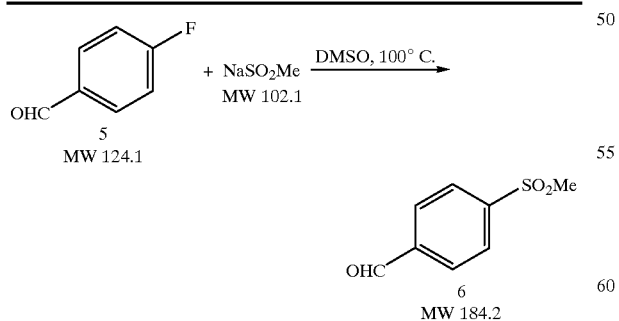

| Materials | Amount | Mol | MW |
|---|---|---|---|
| 4-Fluorobenzaldehyde (5) | 2500 g | 20.1 | 124.1 |
| Sodium methanesulfinate | 2710 g | 26.5 | 102.1 |
| DMSO | 5 L | | |

4-Fluorobenzaldehyde (2.5 kg, 20.1 mol) is dissolved in DMSO (5 L) and sodium methanesulfinate (2.71 kg, 26.5 mol) is added in one portion. The mixture is heated at 100° C.

The reaction is aged for 16 h or until complete. The reaction mixture is poured into cold water (5° C.) (15 L) and aged for 1 h. The solid is filtered and washed with water (10 L). The solid is dried under vacuum with a nitrogen stream. The crude solid is mixed with isopropyl acetate (12 L) and the mixture is heated at 45° C. for 1 h. The slurry is cooled to 25° C. The solid is filtered, washed with isopropyl acetate and suction dried under a nitrogen stream to afford 3.6 kg of the sulfone 6 (97%).

Step 5: Synthesis of Ketosulfone 7

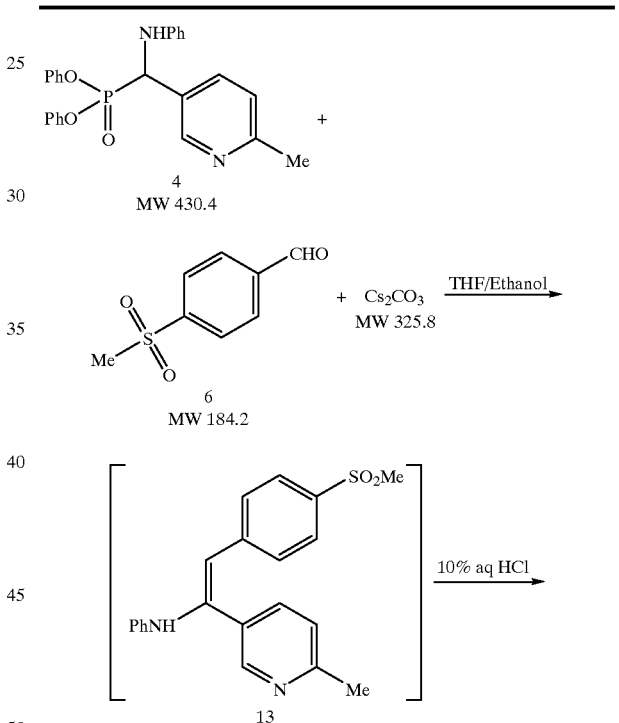

| Materials | Amount | Mol | MW |
|---|---|---|---|
| N,P-Acetal 4 (91 wt %) | 6.21 kg | 13.10 | 430.4 |
| (4-Methylsulfonyl)benzaldehyde (6) | 2.68 kg | 14.55 | 184.2 |
| Cesium carbonate | 5.72 kg | 17.50 | 325.8 |

| | |
|---|---|
| Tetrahydrofuran | 20 L |
| Absolute ethanol | 5 L |
| Hydrochloric acid | 7.5 L |
| Sodium Hydroxide (50%) | 2.5 L |
| Ethyl Acetate | 45 L |
| Hexane | 34 L |
| Water | 56 L |

A 100 L flask is charged with tetrahydrofuran (20 L) and ethanol (5 L) followed by the N,P-acetal 4 (5.64 assay kg, 13.10 mol). (4-Methanesulfonyl)benzaldehyde (6) (2.68 kg, 14.55 mol) is added to the stirred solution.

Cesium carbonate (5.72 kg, 17.50 mol) is added in one portion.

The mixture is stirred until the reaction is complete.

Hydrochloric acid (14 L, 25%) is added over 1 h.

The reaction is stirred until the enamine hydrolysis is complete. The reaction is complete in 2 h.

The solution is diluted with ethyl acetate (30 L) and extracted with 10% aqueous hydrochloric acid (2×12 L; 1×8 L; 1×6 L).

The aqueous extracts are combined and cooled in an ice/methanol bath.

Sodium hydroxide (50%, 2.5 L) is added over 30 min to adjust the pH to 8, whereupon the ketosulfone precipitates.

The mixture is aged for 1 h and the temperature reaches 10° C. The product is filtered, washed with water (10 L) and dried under a stream of nitrogen for 15 h. The solid (4.88 kg) is transferred to a 100 L flask, and ethyl acetate (12 L) and hexanes (27 L) are added. The mixture is heated at 60° C. for 1 h, cooled, and aged at ambient temperature for 3 h. The ketosulfone is filtered, washed with hexanes/ethyl acetate (7:3, 10 L) and dried under vacuum with a stream of nitrogen to afford 2.76 kg (98.3 A %, 97.9 wt %, 72% yield).

Step 6: Preparation of 3-Amino-2-Chloroacrolein (10)

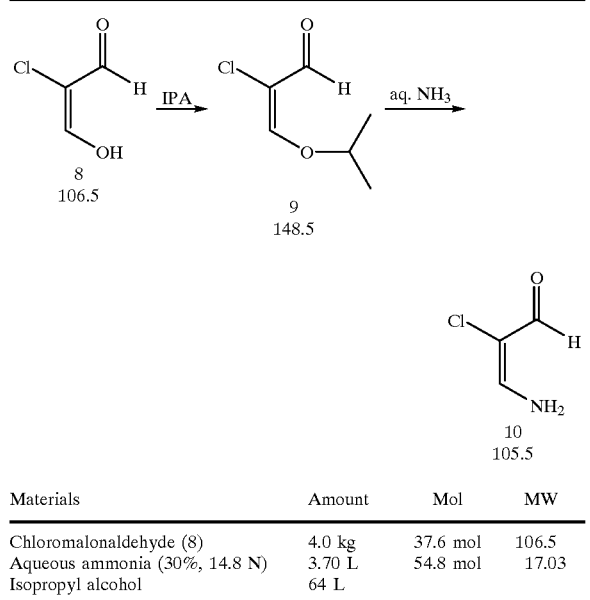

| Materials | Amount | Mol | MW |
|---|---|---|---|
| Chloromalonaldehyde (8) | 4.0 kg | 37.6 mol | 106.5 |
| Aqueous ammonia (30%, 14.8 N) | 3.70 L | 54.8 mol | 17.03 |
| Isopropyl alcohol | 64 L | | |

To a clean 22-L three-necked flask is charged chloromalonaldehyde (6) (4.0 kg, 37.6 mol) and isopropyl alcohol (4 L). The solution is concentrated in a batch concentrator with a continuous, slow feed of isopropyl alcohol (40 L total). The process requires 5 h to complete. The reaction is complete (>95% conversion) as judged by $^1$H NMR.

The resulting dark brown liquid is diluted with isopropyl alcohol (4 L). This mixture is then added over 2 min to a solution of 30% aqueous ammonia (3.7 L) in isopropyl alcohol (20 L) cooled to 5° C. (ice bath cooling) in a 50 L round-bottomed flask.

The reaction solution is warmed to ambient and stirred for 18 h (overnight). The mixture is cooled down to 5° C. using ice bath (3 h). The product is filtered and dried under vacuum with a nitrogen stream to provide 3.12 kg (78%) of the title compound. The filtrate is concentrated to 3 L and the additional product is collected by filtration and dried under vacuum with a nitrogen stream (0.61 kg, 15%). A total of 3.73 kg of product as a brown crystalline solid is obtained (93% overall yield).

Step 7: Preparation of Example 23

Step 7a: Cyclization of Ketosulfone and 3-Amino-2-chloroacrolein

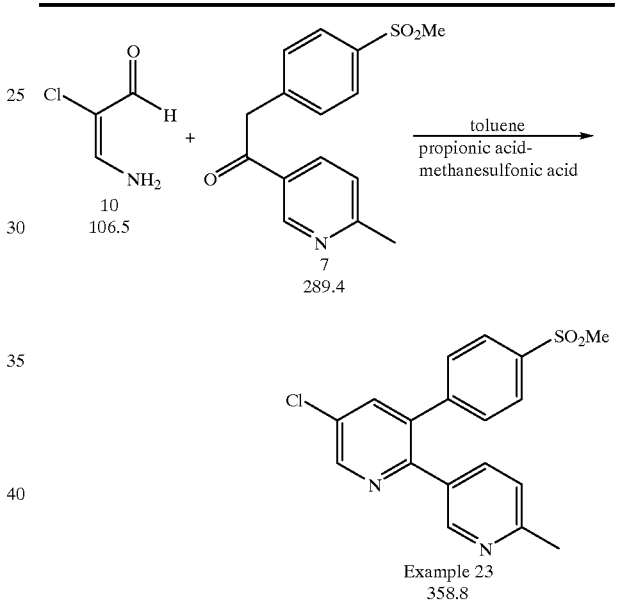

Example 23
358.8

| Materials | Amount | Mol | MW |
|---|---|---|---|
| 3-Amino-2-chloroacrolein (10) | 1.40 kg | 13.1 mol | 106.5 |
| Ketosulfone 7 (98 wt %) | 1.36 kg | 4.69 mol | 289.4 |
| Methanesulfonic acid | 0.992 kg | 10.3 mol | 96.10 |
| n-Propionic acid | 6.9 L | 92.5 mol | 74.08 |
| Ammonium hydroxide (14.8 M) | 6.0 L | 88.8 mol | 17.03 |
| Toluene | 13.5 L | | |
| Isopropyl acetate | 27 L | | |

To a solution of n-propionic acid (4 L) and toluene (8 L) at 75° C. in a 50 L flask is charged ketosulfone 7 (1.385 kg, 4.69 mol) and 3-amino-2-chloroacrolein (10) (1.40 kg, 13.1 mol). Propionic acid (2.9 L, 92.5 mol total), methanesulfonic acid (0.67 L, 10.3 mol), and toluene (5.5 L) are then added. The resulting mixture is heated to reflux (114° C.). The reaction is completed in 13 h at 114° C. as judged by LC (97.5% conversion).

The reaction solution is cooled to ambient and diluted with isopropyl acetate (10 L). Water (10 L) is added and the aqueous phase is neutralized with concentrated ammonium hydroxide solution (6.0 L) to pH 7.2.

The resulting solution is transferred into a 100 L extraction flask, and additional isopropyl acetate (8 L) and water (8 L) are added. The organic layer is washed with a 1:1 mixture of brine/water (2×10 L) and water (10 L). The combined aqueous layers are extracted with isopropyl acetate (9 L).

The combined organic layers are concentrated to a dark brown oil.

Step 7b: Purification of Example 23

Partial Purification of Example 23 Using Hot Extraction

| Materials | |
|---|---|
| | Amount |
| Ethyl acetate | 24 L |
| Hexanes | 96 L |

The crude product from Step 7a is dissolved in ethyl acetate (12 L) in a 72 L flask. The mixture is heated to 50° C., then hexane (48 L) is added while the temperature is maintained at 50° C. The resulting solution is filtered through a pad of Solka-floc (300 g) and the filtrate is set aside.

The Solk-floc cake is washed with ethyl acetate (6 L). This wash is transferred into the same 72 L flask and heated again to 50° C. Hexane (24 L) is added and this mixture is filtered at 50° C. The filtrate is set aside. Ethyl acetate (6 L) and hexane (24 L) are added to the 72 L flask, The mixture is heated to 50° C. and filtered. All three filtrates are combined and concentrated to a brown oil in a batch concentrator. The residue is dissolved in methanol (4 L).

Example 23 HCl Salt Formation

| Materials | | |
|---|---|---|
| | Amount | Mol | MW |
| Hydrogen chloride in ether | 3.2 L | 3.2 mol | 36.5 |
| Ethyl acetate | 5 L | | |
| Methanol | 5 L | | |

The methanol solution of Example 23 is further diluted with ethyl acetate (5 L) and methanol (1 L). A solution of HCl in ether (1.0 M, 3.2 L) is added over 5 min at 25–28° C.

The mixture is aged for 5 min at ambient temperature, cooled to 2° C. over 1 h, and aged for 2 h. The salt is filtered, washed with ethyl acetate (2 L), and dried under vacuum with a nitrogen stream to provide 1.17 kg of Example 23 as the hydrochloride salt (90 wt %, 95% recovery).

Salt Break and Final Crystallization

| Materials | | |
|---|---|---|
| | Amount | Mol | MW |
| 30% Ammonium hydroxide | 2.5 L | 37 mol | 17.03 |
| Isopropyl acetate | 62 L | | |
| Hexanes | 36 L | | |

Three batches of Example 23.HCl (3.37 kg, 90 wt %, 3.03 assayed kg, 7.67 mol) are partitioned between isopropyl acetate (30 L) and water (30 L) in 100 L extraction flask. Concentrated ammonium hydroxide (2.5 L, 37 mol) is added.

The separated organic phase is washed with water (2×15 L).

All three aqueous layers are back-extracted with isopropyl acetate (15 L). The combined organic layers are treated with charcoal (600 g), stirred for 30 min, then filtered through a pad of Solka-Floc. The filtrate is concentrated, dissolved in isopropyl acetate (15 L) at 60° C. and passed through an in-line filter into a 72 L flask. Hexanes (15 L) is added at 60° C., and after several minutes, the product crystallizes. After 40 min additional hexanes (15 L) is added. The mixture is aged for 20 min, cooled from 43° C. to 15° C. over 2.5 h, to 3° C. over 15 min, and aged at 3° C. for 30 min. The solid is filtered, washed with cold isopropyl acetate/hexanes (1:3; 8 L), and dried at room temperature under vacuum with a nitrogen stream to afford 1.92 kg of Example 23.

What is claimed is:

1. A compound of Formula I

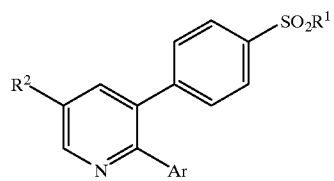

or a pharmaceutically acceptable salt thereof wherein:

$R^1$ is selected from the group consisting of:
(a) $CH_3$,
(b) $NH_2$,
(c) $NHC(O)CF_3$ and
(d) $NHCH_3$;

Ar is a mono-, di-, or tri-substituted pyridinyl or pyridinyl-N-oxide, wherein the substituents are selected from the group consisting of:
(a) hydrogen,
(b) halo,
(c) $C_{1-6}$alkoxy,
(d) $C_{1-6}$alkylthio,
(e) CN,
(f) $C_{1-6}$alkyl,
(g) $C_{1-6}$fluoroalkyl,
(h) $N_3$,
(i) —$CO_2R^3$,
(j) hydroxy,
(k) —$C(R^4)(R^5)$—OH,
(l) —$C_{1-6}$alkyl-$CO_2$—$R^6$ and
(m) $C_{1-6}$fluoroalkoxy;

$R^2$ is selected from the group consisting of:
(a) CN,
(b) $C_{1-6}$fluoroalkyl,
(c) —$CO_2C_{1-6}$alkyl,
(d) —$C(R^8)(R^9)$—OH and
(e) —$C_{1-6}$alkyl-$CO_2$—$R^{10}$; and $R^3$, $R^4$, $R^5$, $R^6$, $R^8$, $R^9$ and $R^{10}$ are each independently selected from the group consisting of:
(a) hydrogen and
(b) $C_{1-6}$alkyl, or $R^4$ and $R^5$ or $R^8$ and $R^9$ together with the atom to which they are attached form a saturated monocyclic ring of 3, 4, 5, 6 or 7 atoms.

2. A compound in accordance with claim 1 wherein $R^2$ represents C1-6 fluoroalkyl.

3. A compound in accordance with claim 1 wherein $R^2$ represents CN.

4. A compound according to claim 2 of formula Ia

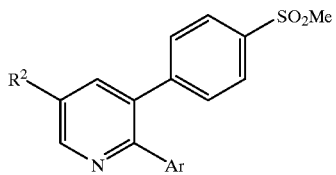

or a pharmaceutically acceptable salt thereof wherein

R² and Ar are selected in accordance with the following table:

|     | R²  | Ar          |
| --- | --- | ----------- |
| (1) | CF₃ | 3-pyr       |
| (2) | CF₃ | 5-(2-Me)pyr |
| (3) | CF₃ | 5-(3-Br)pyr |
| (4) | CF₃ | 5-(3-Cl)pyr |
| (5) | CF₃ | 5-(2-OMe)pyr|
| (6) | CF₃ | 2-(5-Br)pyr.|

5. A compound according to claim 4 wherein the pharmaceutically acceptable salt is an acid salt of citric, hydrobromic, hydrochloric, maleic, methanesulfonic, phosphoric, sulfuric or tartaric acid.

6. A compound according to claim 1 of formula Ib

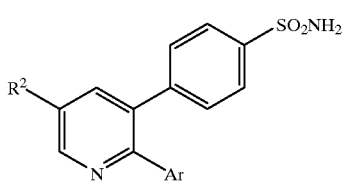

or a pharmaceutically acceptable salt thereof wherein:

R² is CF₃ and

Ar is 3-pyr.

7. A compound according to claim 6 wherein the pharmaceutically acceptable salt is an acid salt of citric, hydrobromic, hydrochloric, maleic, methanesulfonic, phosphoric, sulfuric or tartaric acid.

8. A compound according to claim 2 which is 3-(4-Methylsulfonyl)phenyl-2-(3-pyridinyl)-5-trifluoromethylpyridine.

9. A pharmaceutical composition for the treatment of cyclooxygenase-2 mediated diseases, said composition comprising a compound according to claim 1 and a pharmaceutically acceptable carrier.

10. A compound of formula Ia

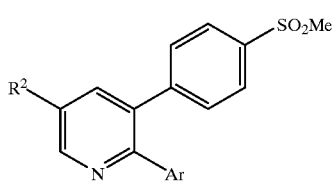

or a pharmaceutically acceptable salt thereof wherein

R² and Ar are selected in accordance with the following table:

|      | R²     | Ar          |
| ---- | ------ | ----------- |
| (1)  | Me     | 3-pyr       |
| (2)  | Cl     | 2-pyr       |
| (3)  | Cl     | 4-pyr       |
| (4)  | Cl     | 5-(3-Br)pyr |
| (5)  | Cl     | 5-(3-Cl)pyr |
| (6)  | Cl     | 5-(2-OMe)pyr|
| (7)  | Cl     | 2-(5-Br)pyr |
| (8)  | F      | 3-pyr       |
| (9)  | F      | 5-(2-Me)pyr |
| (10) | Br     | 3-pyr       |
| (11) | Br     | 5-(2-Me)pyr |
| (12) | NO₂    | 3-pyr       |
| (13) | NO₂    | 5-(2-Me)pyr |
| (14) | OMe    | 3-pyr       |
| (15) | OMe    | 5-(2-Me)pyr |
| (16) | NHCOMe | 3-pyr       |
| (17) | NHCOMe | 5-(2-Me)pyr.|

11. A compound according to claim 10 wherein the pharmaceutically acceptable salt is an acid salt of citric, hydrobromic, hydrochloric, maleic, methanesulfonic, phosphoric, sulfuric or tartaric acid.

12. A compound of formula Ib

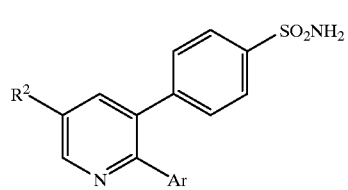

or a pharmaceutically acceptable salt thereof wherein

R² and Ar are selected in accordance with the following table:

|     | R² | Ar            |
| --- | -- | ------------- |
| (1) | Cl | 3-pyr         |
| (2) | Cl | 5-(2-Me)pyr   |
| (3) | Cl | 5-(2-Et)pyr   |
| (4) | Cl | 5-(2-c-Pr)pyr |
| (5) | Cl | 3-(2,6-Me₂)pyr.|

13. A compound according to claim 12 wherein the pharmaceutically acceptable salt is an acid salt of citric, hydrobromic, hydrochloric, maleic, methanesulfonic, phosphoric, sulfuric or tartaric acid.

14. A compound selected from:

5-Methyl-3-(4-methylsulfonyl)phenyl-2-(3-pyridinyl)pyridine;

5-Chloro-3-(4-methylsulfonyl)phenyl-2-(2-pyridinyl)pyridine; and

5-Chloro-3-(4-methylsulfonyl)phenyl-2-(4-pyridinyl)pyridine.

15. A compound according to claim 1 wherein Ar is a mono-, di-, or trisubstituted 2-pyridinyl.

16. A compound according to claim 1 wherein Ar is a mono-, di-, or trisubstituted 3-pyridinyl.

17. A compound according to claim 1 wherein $R^1$ is $CH_3$ or $NH_2$.

18. A compound according to claim 1 wherein Ar is a mono-, di-, or trisubstituted 2-pyridinyl or 3-pyridinyl and the substituents are selected from the group consisting of:
  (a) hydrogen,
  (b) halo,
  (c) $C_{1-3}$alkoxy,
  (d) $C_{1-3}$alkylthio,
  (e) $C_{1-3}$alkyl,
  (f) $CF_3$ and
  (g) CN.

19. A compound according to claim 1 wherein $R^1$ is $CH_3$ or $NH_2$; and

Ar is a mono-, di-, or trisubstituted 2-pyridinyl or 3-pyridinyl and the substituents are selected from the group consisting of:
  (a) hydrogen,
  (b) halo,
  (c) $C_{1-3}$alkoxy,
  (d) $C_{1-3}$alkylthio,
  (e) $C_{1-3}$alkyl,
  (f) $CF_3$ and
  (g) CN.

* * * * *